US 7,954,486 B2

(12) United States Patent
Papania et al.

(10) Patent No.: US 7,954,486 B2
(45) Date of Patent: Jun. 7, 2011

(54) AEROSOL DELIVERY SYSTEMS AND METHODS

(75) Inventors: Mark J. Papania, Lilburn, GA (US);
James J. Barry, Hanover, NH (US);
Mark C. Bagley, Grafton, NH (US);
Nabil A. Elkouh, Meriden, NH (US);
Darin Knaus, Norwich, VT (US);
Robert Trabka, Newport, NH (US)

(73) Assignees: The United States of America as represented by the Secretary of the Department of Health and Human Services, Washington, DC (US); Centers for Disease Control and Prevention, Atlanta, GA (US); Creare Inc., Hanover, NH (US)

( * ) Notice: Subject to any disclaimer, the term of this patent is extended or adjusted under 35 U.S.C. 154(b) by 1348 days.

(21) Appl. No.: 10/587,814

(22) PCT Filed: Apr. 1, 2005

(86) PCT No.: PCT/US2005/011086
§ 371 (c)(1),
(2), (4) Date: Jul. 28, 2006

(87) PCT Pub. No.: WO2006/006963
PCT Pub. Date: Jan. 19, 2006

(65) Prior Publication Data
US 2009/0223513 A1   Sep. 10, 2009

Related U.S. Application Data

(60) Provisional application No. 60/559,318, filed on Apr. 2, 2004.

(51) Int. Cl.
*A61M 11/00* (2006.01)
*A61M 15/00* (2006.01)
*B05B 17/06* (2006.01)

(52) U.S. Cl. .............................. 128/200.14; 128/200.16
(58) Field of Classification Search ........... 128/200.11–200.24, 203.12, 203.15, 128/203.25, 204.14; 222/206–212, 214, 222/215; 239/102.1, 102.2
See application file for complete search history.

(56) References Cited

U.S. PATENT DOCUMENTS
318,930 A    5/1885   Sutton
(Continued)

FOREIGN PATENT DOCUMENTS
DE    40 19 656 A1    3/1991
(Continued)

OTHER PUBLICATIONS

The International Search Report and the Written Opinion of the International Searching Authority of PCT Application No. PCT/US2005/011086.

(Continued)

*Primary Examiner* — Justine R Yu
*Assistant Examiner* — Valerie Skorupa
(74) *Attorney, Agent, or Firm* — Klarquist Sparkman, LLP

(57) ABSTRACT

Methods and systems for aerosol delivery of agents to a patient are described herein. The present system can be used to administer various types of agents, such as a vaccine or other types of pharmaceutical substances. Certain embodiments of the present system utilize an actuator coupled to a disposable aerosolizing element that aerosolizes an agent for delivery to a patient when acted upon by the actuator. The aerosolizing element prevents the agent from contacting the actuator and other non-disposable components of the system so that little or no cleaning or maintenance is required. The present system also can include an aerosolization rate monitor that monitors the rate at which an agent is being aerosolized and provides feedback to the user to ensure that the proper dose is being administered.

30 Claims, 17 Drawing Sheets

U.S. PATENT DOCUMENTS

| | | | |
|---|---|---|---|
| 2,908,479 A | | 10/1959 | Goodspeed, Jr. |
| 3,561,444 A | | 2/1971 | Boucher |
| 3,612,049 A | * | 10/1971 | Monson .................. 128/203.19 |
| 3,861,386 A | | 1/1975 | Harris et al. |
| 4,036,223 A | | 7/1977 | Obert |
| 4,106,503 A | | 8/1978 | Rosenthal et al. |
| 4,117,844 A | | 10/1978 | James |
| 4,286,636 A | | 9/1981 | Credle |
| 4,319,155 A | | 3/1982 | Nakai et al. |
| 4,647,013 A | * | 3/1987 | Giachino et al. ............. 251/331 |
| 4,756,347 A | | 7/1988 | Hagan et al. |
| 4,877,989 A | | 10/1989 | Drews et al. |
| 4,945,929 A | * | 8/1990 | Egilmex ........................ 131/273 |
| 5,063,922 A | | 11/1991 | Häkkinen |
| 5,186,057 A | * | 2/1993 | Everhart .................... 73/861.41 |
| 5,215,079 A | | 6/1993 | Fine et al. |
| 5,261,601 A | | 11/1993 | Ross et al. |
| 5,299,739 A | | 4/1994 | Takahashi et al. |
| 5,443,059 A | | 8/1995 | Koch et al. |
| 5,447,151 A | * | 9/1995 | Bruna et al. ............. 128/203.15 |
| 5,499,972 A | | 3/1996 | Parsons |
| 5,515,841 A | | 5/1996 | Robertson et al. |
| 5,515,842 A | | 5/1996 | Ramseyer et al. |
| 5,544,646 A | | 8/1996 | Lloyd et al. |
| 5,551,416 A | | 9/1996 | Stimpson |
| 5,660,166 A | | 8/1997 | Lloyd et al. |
| 5,704,911 A | | 1/1998 | Parsons |
| 5,709,202 A | | 1/1998 | Lloyd et al. |
| 5,758,637 A | | 6/1998 | Ivri et al. |
| 5,803,362 A | | 9/1998 | Fraccaroli |
| 5,826,571 A | | 10/1998 | Casper et al. |
| 5,848,587 A | | 12/1998 | King |
| 5,879,327 A | | 3/1999 | Moreau DeFarges et al. |
| 5,891,086 A | | 4/1999 | Weston |
| 5,921,232 A | | 7/1999 | Yokoi et al. |
| 5,950,619 A | | 9/1999 | van der Linden et al. |
| 5,970,974 A | | 10/1999 | Van Der Linden et al. |
| 5,996,903 A | | 12/1999 | Asai et al. |
| 6,026,807 A | | 2/2000 | Puderbaugh et al. |
| 6,116,237 A | | 9/2000 | Schultz et al. |
| 6,123,068 A | | 9/2000 | Lloyd et al. |
| 6,125,844 A | | 10/2000 | Samiotes |
| 6,158,431 A | | 12/2000 | Poole |
| 6,196,218 B1 | | 3/2001 | Voges |
| 6,196,219 B1 | * | 3/2001 | Hess et al. ............... 128/200.21 |
| 6,273,342 B1 | | 8/2001 | Terada et al. |
| 6,363,932 B1 | | 4/2002 | Forchione et al. |
| 6,405,934 B1 | * | 6/2002 | Hess et al. ......................... 239/4 |
| 6,550,472 B2 | | 4/2003 | Litherland et al. |
| 6,651,650 B1 | | 11/2003 | Yamamoto et al. |
| 6,676,034 B2 | | 1/2004 | Tanaka et al. |
| 6,851,626 B2 | | 2/2005 | Patel et al. |
| 2002/0020408 A1 | | 2/2002 | Knauer |
| 2002/0124852 A1 | * | 9/2002 | Gonda et al. ................... 128/898 |
| 2002/0134372 A1 | | 9/2002 | Loeffler et al. |
| 2002/0195100 A1 | | 12/2002 | Webb |
| 2003/0164169 A1 | | 9/2003 | Stangl et al. |
| 2003/0205226 A1 | * | 11/2003 | Gallem et al. ........... 128/200.14 |
| 2004/0055596 A1 | | 3/2004 | Bacon |
| 2005/0011514 A1 | | 1/2005 | Power et al. |
| 2005/0199236 A1 | | 9/2005 | Fink et al. |
| 2005/0205089 A1 | | 9/2005 | Fink et al. |

FOREIGN PATENT DOCUMENTS

| | | | |
|---|---|---|---|
| EP | 0 646 385 | A1 | 4/1995 |
| EP | 0729764 | A1 | 9/1996 |
| EP | 1 149 602 | | 10/2001 |
| EP | 1201258 | A2 | 5/2002 |
| EP | 0701457 | | 12/2003 |
| GB | 2272389 | A | 5/1994 |
| JP | 061068159 | | 4/1986 |
| JP | 5-44257 | | 6/1993 |
| JP | 07080369 | | 3/1995 |
| JP | 08196965 | | 8/1996 |
| JP | 2000233158 | | 8/2000 |
| JP | 2001149473 | | 6/2001 |
| JP | 2001149833 | | 6/2001 |
| JP | 2001149834 | | 6/2001 |
| WO | WO96/13293 | | 5/1996 |
| WO | WO 00/58022 | | 10/2000 |
| WO | WO01/76762 | A2 | 10/2001 |
| WO | WO 02/074372 | | 9/2002 |
| WO | WO 02074372 | A2 * | 9/2002 |

OTHER PUBLICATIONS

Co-pending U.S. Appl. No. 10/471,620.
Cutts et al., "Alternative Routes of Measles Immunization: a Review," *Biologicals* 25(3):323-338 (1997).
Dhand, "Nebulizers that Use a Vibrating Mesh or Plate with Multiple Apertures to Generate Aerosol," *Respir. Care* 47:1406-1416 (2002).
Dixon, "Sound Medicine," *British Medical Journal (International)* 311:1030 (1995).
Greenspan B.J., "Ultrasonic and Electrohydrodynamic Methods for Aerosol Generation," in Hickey, AJ, ed., *Inhalation Aerosols: Physical and Biological Basis for Therapy*, New York, Marcel Dekker, Inc., 1996.
Grossman J., "The Evolution of Inhaler Technology," *J. Asthma* 31:55-64 (1994).
Harvey et al., "Comparison of Jet and Ultrasonic Nebulizer Pulmonary Aerosol Deposition During Mechanical Ventilation," *Eur. Respir. J. 10*:905-909 (1997).
Holzner et al., "Characterization of Particle Size and Microbiological Properties of a Novel Low Frequency Ultrasonic Nebulizer," Proc. 2nd World Meeting APGI/APV, Paris, May 25-28, 1998, pp. 953-954.
Lefebvre, A.H., *Atomization and Sprays*, New York, Hemisphere, p. 264-272, 1989.
Niven, R.W., Atomization and Nebulizers, in Hickey, A.J., ed., *Inhalation Aerosols: Physical and Biological Basis for Therapy*, New York, Marcel Dekker, Inc., 1996.
Drug Delivery Systems—Pulmonary: Part 5, in *Medical & Healthcare Marketplace Guide*, v.1, p. I-376+, 1998).
Office Action from the United States Patent & Trademark Office in co-pending U.S. Appl. No. 10/471,620, dated Sep. 22, 2006.
Notice of Reasons for Rejection from the Japan Patent Office, for Japanese Patent Application No. 2007-506310, dated Jun. 30, 2010.
European Patent Office, "Communication—European Search Report" for European Application No. EP10008772.5-2320, Oct. 29, 2010, 9 pages.

* cited by examiner

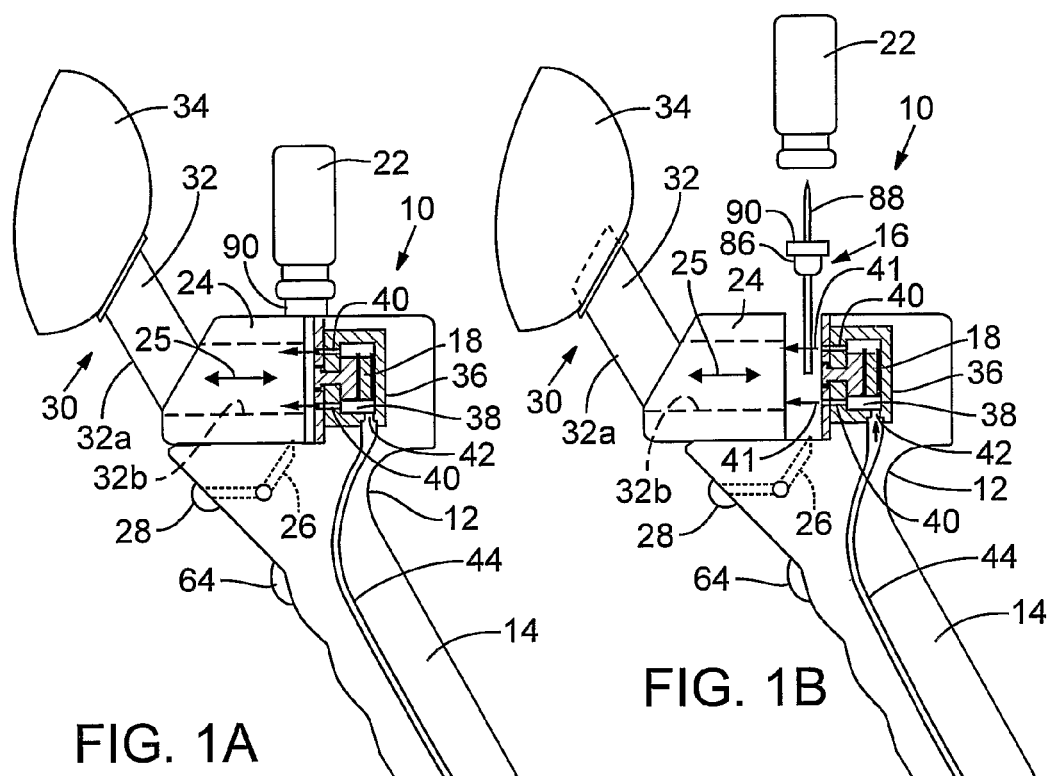
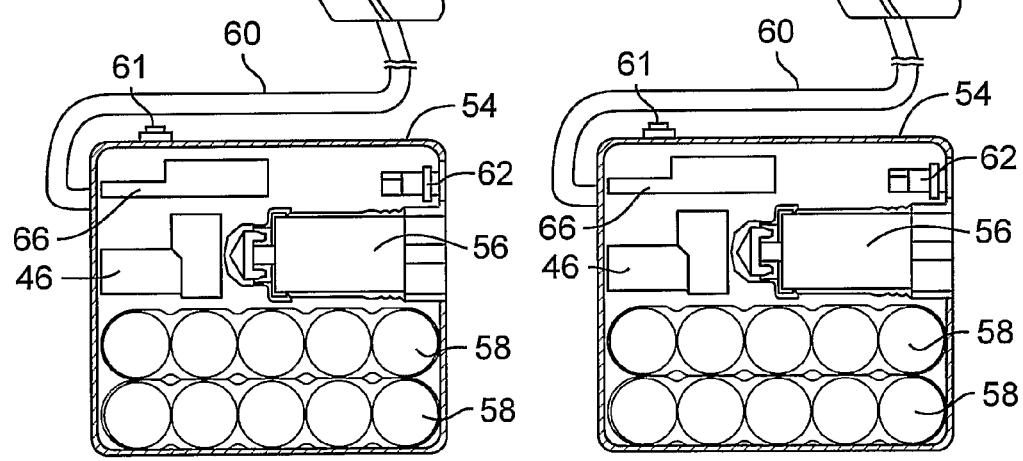
FIG. 1A
FIG. 1B

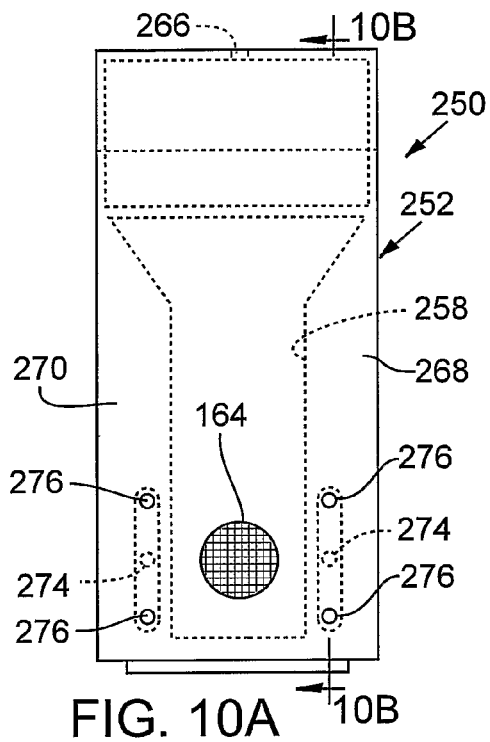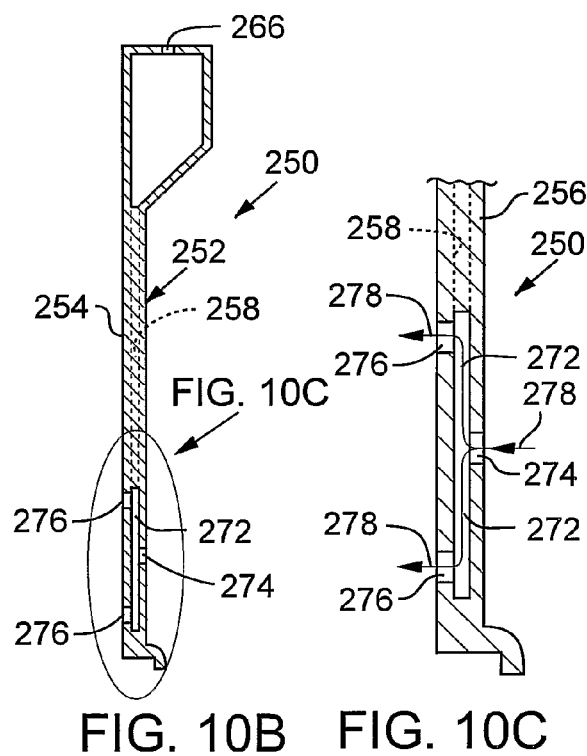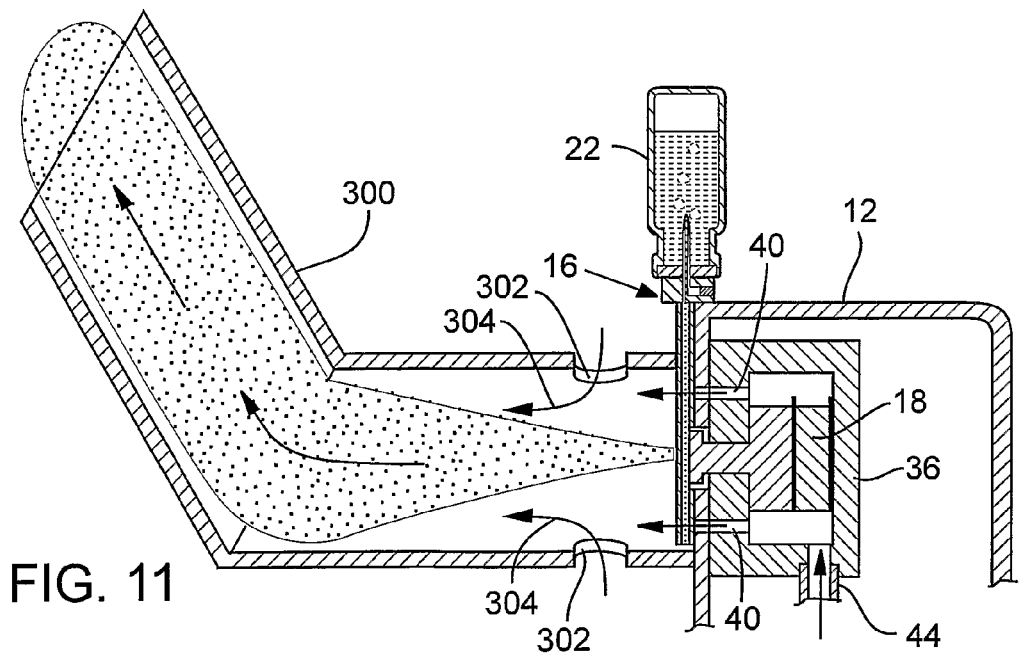

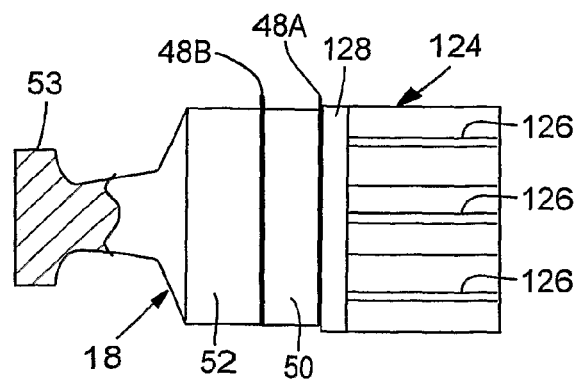
FIG. 21A
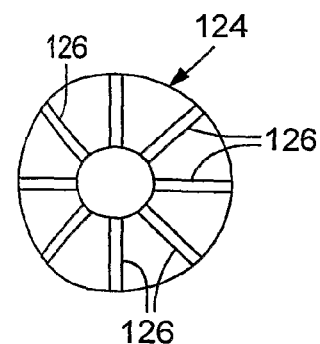
FIG. 21B
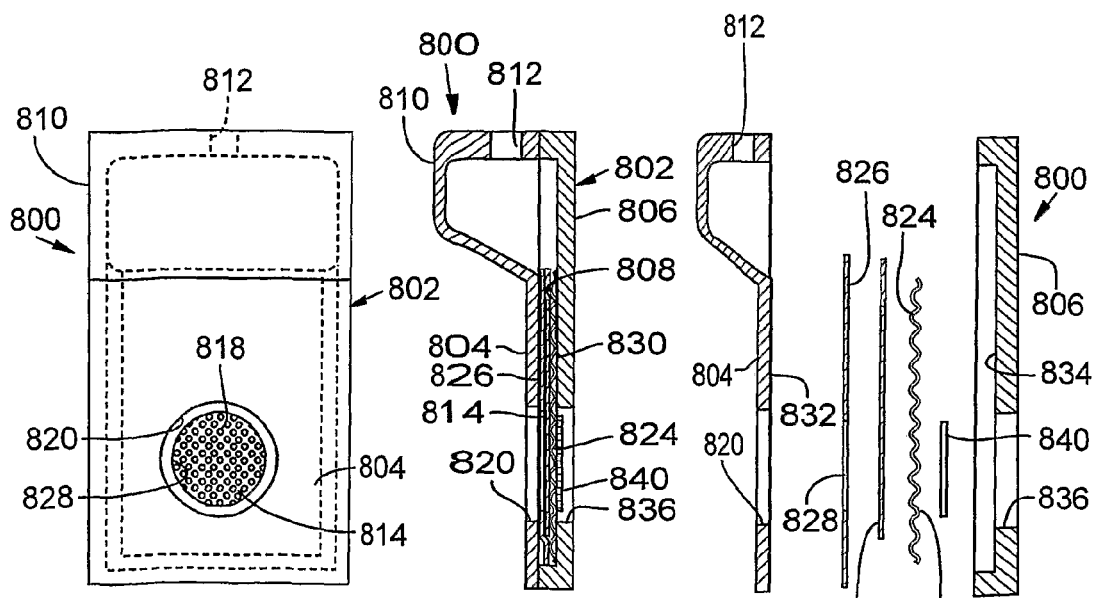
FIG. 22A
FIG. 22B
FIG. 22C

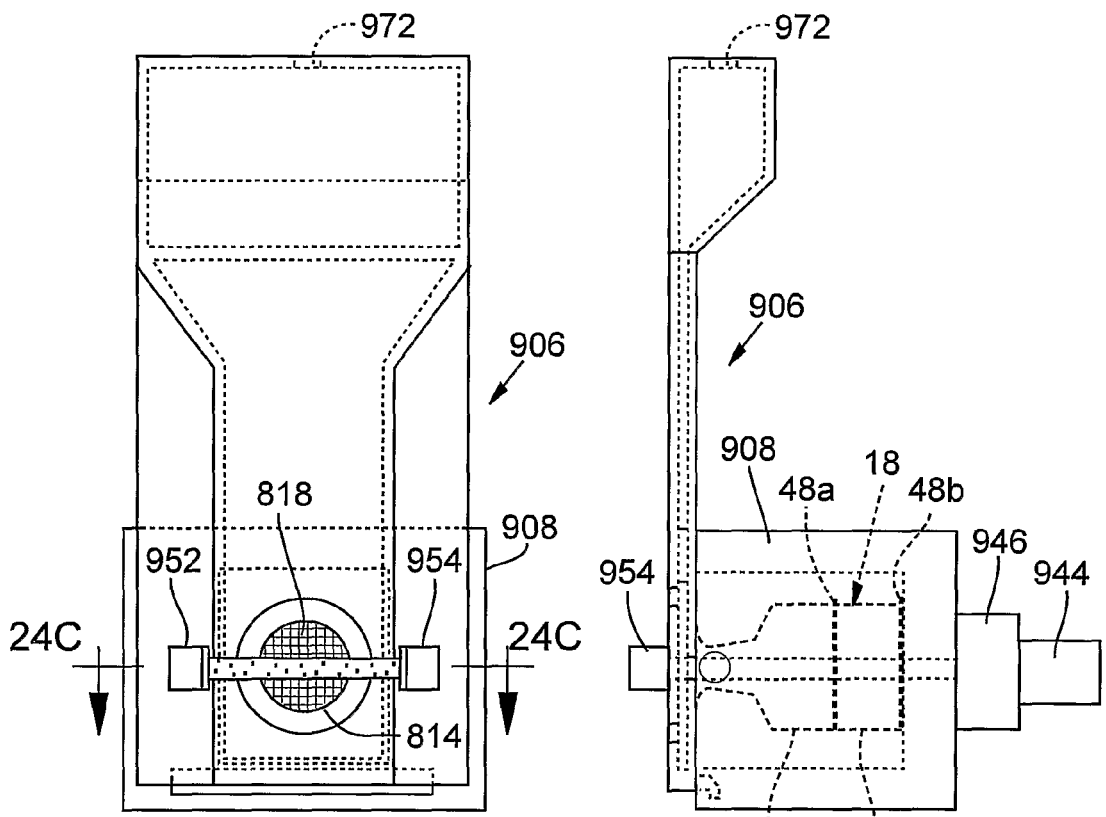
FIG. 24A
FIG. 24B
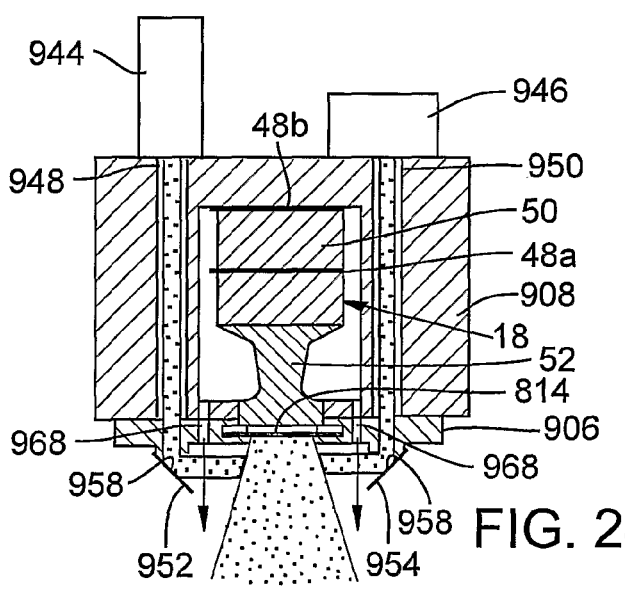
FIG. 24C

AEROSOL DELIVERY SYSTEMS AND METHODS

CROSS REFERENCE TO RELATED APPLICATION

This is the U.S. national stage application of PCT Application No. PCT/US2005/011086, filed Apr. 1, 2005, which claims the benefit of U.S. Provisional Application No. 60/559,318, filed Apr. 2, 2004, which is incorporated herein by reference.

GOVERNMENT INTERESTS

This invention was made by the Centers for Disease Control and Prevention, an agency of the United States Government. Therefore, the United States Government may have certain rights in this invention.

FIELD

The present disclosure relates generally to the delivery of agents, and more particularly, to systems and methods for delivery of agents using aerosol devices.

BACKGROUND

Needles and syringes have posed a variety of problems for patients and medical personnel who administer agents to the patients, including injection safety, needle stick injury, disposal problems, transmission of blood borne diseases, and needle shortages during mass vaccination campaigns. The replacement of needles and syringes as the primary delivery vehicle for agents has the potential for tremendous cost savings, increased safety and reduction of biomedical wastes.

Aerosol delivery of agents avoids many of the foregoing drawbacks of injection. Much of the equipment used for aerosol delivery is cumbersome and has not been widely employed for many treatment methods. Nebulizers are commonly used in hospitals for aerosol delivery of agents in the treatment of respiratory diseases. In practice, a nebulizer uses compressed gases to convert a solution of the agent into fine droplets. The droplets are administered to the patient through an air stream that the patient breathes inwardly through a mouthpiece or mask. As the patient breathes, the agent is delivered to the patient's lungs and absorbed therein.

Typically, nebulizers rely upon an external compressed gas source to convert a solution of the agent into fine droplets. As a result of the need for an external source of compressed gas, nebulizers tend to be bulky and difficult to move. Further, the effectiveness of a nebulizer depends upon proper inhalation by the patient, which can be difficult to monitor and to teach to the patient.

Currently used jet nebulizers function in the same general way. Liquid is drawn up to an air nozzle by capillary forces and/or the Bernoulli effect. At the nozzle, a high-speed air jet shatters the liquid into droplets. Droplets blast against an impactor to break them up further into smaller droplets. Like most atomization processes, this droplet generation process results in a size distribution. To obtain the desired small aerosol droplets, baffles capture large droplets (which cannot follow the airflow path well), leaving the fine aerosol in the output stream of the nebulizer. The larger droplets recycle to the liquid reservoir of the nebulizer.

This nebulization process is inherently inefficient. Measurements show that typical nebulizers only convert a few percent of the aspirated liquid to fine aerosol droplets. Thus, liquid will normally be recycled well in excess of twenty times before it reaches the desired size and is exhausted from the nebulizer. The inefficiency of the jet nebulizer poses problems to its use for aerosol vaccination. High velocity is needed in the air jet to provide the energy required to break the liquid into sufficiently small droplets, necessitating relatively high air supply pressures in flow rates. Compressing air to provide this supply requires significant power, either human or electric.

Fluid recycling in the nebulizer in the small amount of vaccine required for each dose results in the inability to operate on a dose-by-dose basis. Many doses need to be present in the nebulizer in order for droplet coalescence on the baffles in other surfaces to return liquid to the reservoir. In addition, the repeated mechanical stress of atomization on the vaccination particles in the liquid risks diminishing the viability of the vaccine.

Another drawback of conventional nebulizers is that the components that come in contact with the agent being dispensed must be thoroughly cleaned after each session of use to prevent the growth of bacteria or other contaminants. Such cleaning and maintenance requirements pose a modest challenge in modern medical settings, but can prove to be extremely difficult to achieve with untrained personnel or in underdeveloped regions of the world. Hence, conventional nebulizers are impractical for use in mass vaccination campaigns, especially in underdeveloped countries.

Existing vibrating mesh nebulizers have similar drawbacks. Vibrating mesh devices typically operate by ejecting droplets through tiny orifices of a thin plate (the "mesh") that is vibrated ultrasonically by an actuator. Existing vibrating mesh devices place the agent to be aerosolized in direct contact not only with the mesh, but also with the actuator. In such devices, the mesh, actuator surfaces, and the fluid pathway in the device are intended for long-term single-patient use and must be cleaned after each use. Cleaning of these devices under field conditions and their use in multi-patient settings, such as in mass vaccination campaigns impose substantial difficulties and costs.

Monitoring or verifying the dose of aerosol delivered to a patient also poses a concern in the administration of aerosols (e.g., aerosol vaccination), especially when young children are involved. Unlike injection, where the delivery of a dose can be clearly observed, the delivery of an aerosolized agent via a nebulizer is more difficult to monitor.

Thus, a need exists for effective systems and methods for administering an agent in an aerosol form, without a needle, and in more accurate dosages. Further, a need exists for delivery systems that are easier to use and maintain and reduce the likelihood of contamination, especially for use in mass vaccination campaigns.

SUMMARY

The present disclosure concerns methods and systems, including devices, for delivery of agents that do not require use of needles to gain entry into a biological system. More particularly, the present disclosure concerns methods and systems for aerosolizing, or nebulizing, agents for patient delivery. For example, such systems and methods can be used for delivering agents such as pharmaceuticals, chemotherapeutics, immune agents, and vaccines.

The present disclosure describes methods and systems for administering one or more agents to multiple patients (either human or non-human) in single dosage applications or to an individual patient for multiple administrations. For example, many patients can be immunized with an inhaled vaccine composition using the present disclosure without the need for needles or substantial cleaning or maintenance. In other applications, the composition may be administered to one individual.

An embodiment of the present disclosure comprises a portable aerosol delivery device that includes a housing shaped to be held in a user's hand. The housing houses a disposable aerosolization element and an actuator that is operable to apply a moving force to the aerosolization element for aerosolizing an agent The aerosolization element can include an integral reservoir in which there is stored a predetermined volume of agent.

Alternatively, the aerosolization element can be directly coupled to a vial or container in which the agent is stored. For example, the aerosolization element can include a piercing prong or needle that is inserted into a puncturable closure (e.g., a rubber cap) of a vial to allow agent stored in the vial to flow into the aerosolization element. The amount of agent stored in the aerosolizing element and/or the vial can be sufficient for administering a single dose or multiple doses of the agent.

The aerosolization element defines an internal chamber that receives agent from the reservoir and/or a vial coupled to the aerosolization element. One side of the chamber is partially bounded by an orifice surface defining a plurality of orifices. The opposite side of the chamber is partially bounded by a movable element that is coupled to the actuator. Vibratory oscillations of the actuator cause the movable element to move alternately toward and away from the orifice surface. As the movable element moves closer to the orifice surface, the pressure in the chamber increases and causes the agent to be expelled through the orifices in the form of aerosol droplets. As the movable element moves away from the orifice surface, additional agent is drawn into the chamber to be aerosolized in the next cycle. When the aerosolization element (or the vial connected to the aerosolization element) is empty, the aerosolization element can be removed for disposal and replaced with another aerosolization element.

Agent can be fed into the chamber of the aerosolization element either through gravity or capillary action. In the case of gravity feed, the agent is stored in the reservoir and/or a vial positioned above the chamber so that agent can flow into the chamber under the force of gravity. In the case of capillary feed, the agent is stored in the reservoir and/or a vial positioned below the chamber and is drawn upwardly into the chamber by capillary action of the agent.

Advantageously, the aerosolization element prevents the agent from contacting the actuator and other non-disposable components of the device so that little or no cleaning or flushing of the device is required after each session. Consequently, unlike conventional nebulizers, the device of the present disclosure is suitable for use in high-workload applications, such as mass immunization campaigns in underdeveloped nations. Use of the aerosol delivery device also avoids many of the drawbacks of administering agents via injection, including the need for skilled personnel, the risk of blood-borne diseases, high cost, patient aversion to injection, and the need to safely dispose of used needles and syringes.

In particular embodiments, the aerosol delivery device also includes an aerosolization rate monitor that monitors the rate at which the agent is being aerosolized. The aerosolization monitor includes a light source, such as a laser diode, for projecting a light beam across an aerosol plume emanating from the aerosolization element. A light detector, such as a photodiode, detects the obscuration of the light beam, which corresponds to the concentration of aerosol droplets in the aerosol plume. The device can include a visual display, such as a digital readout, that displays the aerosolization rate to ensure that the proper dosage is being administered. The device also can include an indicator light and/or an audible alarm for warning the user when the aerosolization rate is outside an acceptable range.

The aerosol delivery device includes a patient interface that delivers the aerosolized agent to the mouth and/or nose of a patient. One embodiment of the patient interface includes an angled extension portion coupled to the housing of the device and a disposable face mask that is shaped to cover the mouth and nose of the patient. In one implementation, the mask is made of a porous material that allows expiratory and inspiratory air to pass through the mask, but traps expired aerosol and particles (e.g., cough or sneeze particles). In another implementation, the mask is made of a non-porous material and the extension portion is formed with one or more openings allowing inspiratory air to be drawn into the extension portion.

Another embodiment of the patient interface includes a one-way valve that is operable to permit aerosolized agent to flow to the patient and restrict flow in the opposite direction. The one-way valve can be, for example, a flapper-type valve or "duckbill" type valve. The valve protects the aerosolization element and other revisable components against contamination caused by expired particles. In addition, the entire patient interface is disposable to further protect against patient-to-patient contamination.

The foregoing and other objects, features, and advantages of the invention will become more apparent from the following detailed description, which proceeds with reference to the accompanying figures.

BRIEF DESCRIPTION OF THE DRAWINGS

FIGS. 1A and 1B are side views, shown partially in section, of an aerosol delivery device, according to one embodiment.

FIG. 10A is a front elevation view of another embodiment of an aerosolization element for an aerosol delivery device.

FIG. 10 is a cross-sectional view taken along line 10B-10B of FIG. 10A. FIG. 10C is a magnified cross-sectional view of a portion of the aerosolization element.

FIG. 11 is an enlarged cross-sectional view of a patient interface shown being used with the aerosol delivery device of FIGS. 1A and 1B.

FIG. 21A is a side elevation view of a piezoelectric actuator for an aerosol delivery device and a heat sink coupled to the actuator. FIG. 21B is an end view of the heat sink shown in FIG. 21A.

FIGS. 22A, 22B, and 22C are front elevation, cross-sectional, and exploded views of an aerosolization element, according to another embodiment.

FIGS. 24A and 24B are front and side elevation views, respectively, of components of the aerosol delivery device shown in FIG. 23. FIG. 24C is a cross-sectional view taken along line 24C-24C of FIG. 24A.

DETAILED DESCRIPTION

Figure 2:
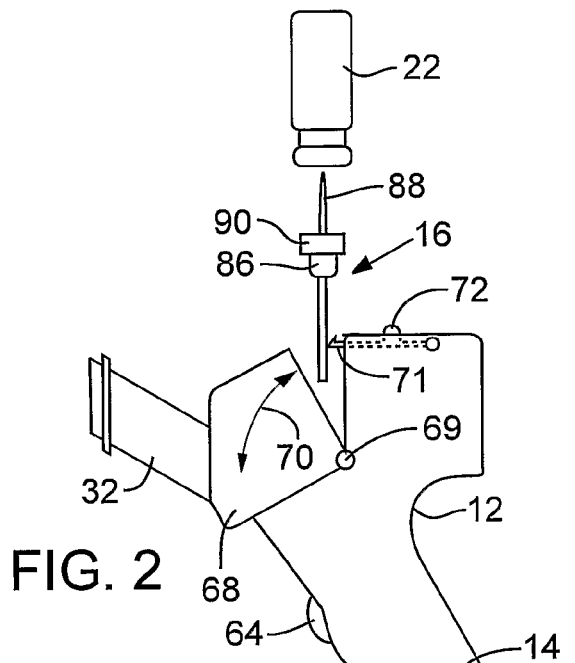
FIG. 2 is a side view of an aerosol delivery device, according to another embodiment.

As used herein, the singular forms "a," "an," and "the" refer to one or more than one, unless the context clearly dictates otherwise.

As used herein, the term "includes" means "comprises."

Agents, as used herein, comprise agents that can be administered to living organisms for an effect in the treated organism. Such agents include live and killed organisms for vaccination, immunogens, immune activators or suppressors, chemotherapeutics, pharmaceuticals, nucleic acids, insulin, hormones, antibodies and fragments thereof, receptors, proteins, carbohydrates, fats, nutrients, anesthetics, narcotics, and pain relievers.

The present disclosure is directed to methods and systems, including devices, for aerosol delivery of agents to a patient. The present system can be used to administer various types of agents, such as vaccines and other pharmaceutical substances. Use of the present system for agent delivery, such as for vaccination purposes, provides many benefits. For example, the present system replaces the use of needles and syringes, and reduces the costs of agent delivery. Additionally, the present system allows for treatment of patients by less-trained staff, another cost saving benefit, and also helps prevent the spread of blood borne diseases by reused needles.

Certain embodiments of the present system utilize an actuator coupled to a disposable aerosolizing element that aerosolizes an agent for delivery to a patient when acted upon by the actuator. The aerosolizing element prevents the agent from contacting the actuator and other non-disposable components of the system so that little or no cleaning or maintenance is required. The system therefore is well suited for use by less-trained personnel in high-workload applications, such as mass vaccination campaigns.

The present system also can include an aerosolization rate monitor that monitors the rate at which an agent is being aerosolized and provides feedback to the user to ensure that the proper dose is being administered. For example, the system can include an indicator light that illuminates or flashes if the aerosolization rate is outside an acceptable range.

Exemplary methods of the present disclosure comprise delivery of agents such as vaccine compositions. The methods of the present disclosure comprise delivery of vaccine compositions via aerosol administration. The present disclosure contemplates the use of any vaccine composition that can be delivered via aerosol administration. Particularly preferred vaccination compositions are those for measles, mumps and rubella. Such compositions may comprise measles vaccine, mumps vaccine, rubella vaccine and combinations and mixtures such as measles and mumps, rubella and mumps, measles and rubella, and measles, mumps and rubella. The vaccines further comprise pharmaceutical or formulation components such as those known in the art, including, but not limited to, diluents, compounding agents, surfactants, and agents to maintain sterility.

FIGS. 1A and 1B depict an aerosol delivery device 10, according to one embodiment. The aerosol delivery device 10, includes a body, or housing 12 formed with a handle portion 14 shaped to be held in a user's hand. The housing 12 in the illustrated embodiment houses a removable aerosolizing element 16, an actuator 18, and an air manifold 36 substantially surrounding the actuator 18. The illustrated aerosolizing element 16 is directly coupled to a vial 22 containing an agent (e.g., a vaccine) to be administered to a patient. As described in detail below, the aerosolizing element 16 receives the agent from the vial 22 and expels aerosol droplets through orifices 110 (FIG. 4A) for delivery to a patient upon activation of the actuator 18.

The housing 12 is formed with a movable front portion 24 that is mounted for sliding movement in the directions indicated by double-headed arrow 25 between a closed position (as shown in FIG. 1A) and an open position (as shown in FIG. 1B) to allow access to the aerosolizing element 16. When the front portion 24 is in the closed position, the aerosolizing element 16 is held firmly in place between the front portion and the actuator 18. A latch mechanism 26 and a latch button 28 can be provided to releasably retain the front portion 24 in the closed position. Depressing the latch button 28 removes the latch mechanism 26 from engagement with the front portion 24 so that it can be moved to the open position. The front portion 24 desirably is adapted to be completely removable from the housing 12 for ease of cleaning. While the illustrated front portion 24 is mounted for sliding movement relative to the housing 12 as shown, any other detachable connection can be used to mount the front portion 24 to the housing (e.g., adhesives, snap fittings, etc.).

Coupled to the housing 12 is a patient interface 30 for delivering an aerosolized agent to a patient. The illustrated patient interface 30 includes a generally cylindrical extension portion 32 connected to the movable portion 24 and a disposable face mask 34 mounted to the upper end of the extension portion 32. The mask 34 is mounted to the extension portion 32 in a removable manner so that the mask can be easily removed and replaced with a new mask for another patient. The extension portion 32 includes a first portion 32*a* extending through the front portion 24 of the housing 12 and a second portion 32*b* that extends upwardly at an angle with respect to the first portion 32*a*. The extension portion 32 may be of a rigid or flexible design and desirably is constructed from a low cost material, such as rubber, cardboard, fiberboard or plastic.

Figure 4A:
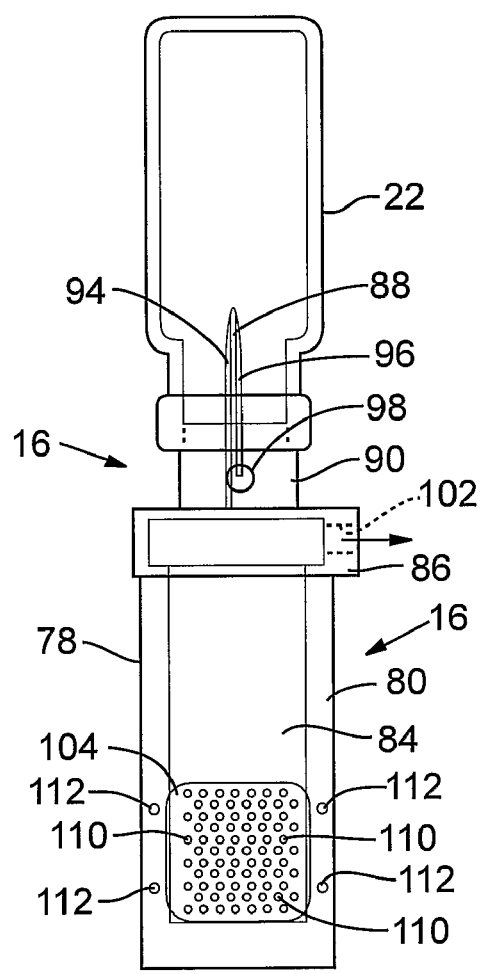
FIGS. 4A and 4B are front elevation and cross-sectional views, respectively, of a removable and disposable aerosolization element for an aerosol delivery device, according to one embodiment.

Generally, contaminants (e.g., expired particles from the patient) are difficult to re-aerosolize unless they directly contact the surface of the aerosolizing element 16 adjacent the orifices 110 (FIG. 4A). The angled second portion 32*b* eliminates a direct pathway from the patient back to the aerosolizing element so as to prevent expired particles (e.g., cough and sneeze particles) from directly contacting the aerosolizing element 16. Hence, this protects against patient-to-patient contamination if the aerosolizing element 16 is used to administer doses to multiple patients. The face mask 34 can be made from a porous or non-porous material, as further described below. Other types of non-disposable or disposable patient interfaces, such as nasal prongs, oral mouthpieces, and holding chambers, also can be used with the aerosol delivery device 10.

Figure 4B:
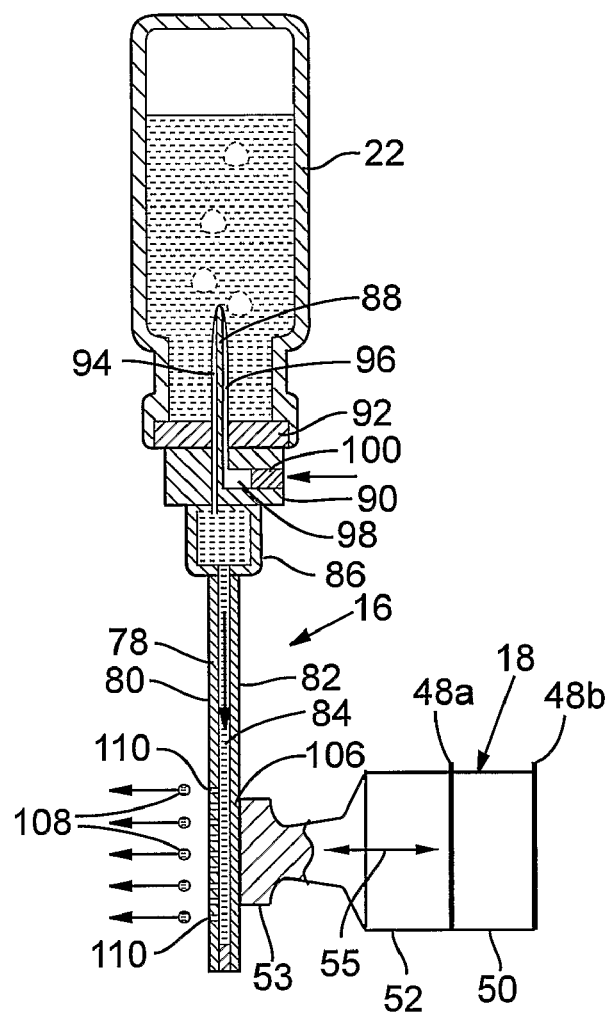

The actuator 18 is operable to apply a moving force to the aerosolizing element 16, thereby causing the aerosolizing element to expel aerosol droplets of an agent. The actuator 18 can be any type of oscillator that can apply vibratory oscillations to the aerosolizing element 16. As best shown in FIG. 4B, the illustrated actuator 18 is a piezoelectric-driven actuator (also known as an ultrasonic horn) that includes first and second electrodes 48*a*, 48*b*, a piezoelectric element 50 disposed between the first and second electrodes, and a motion transmitting member 52 secured to the first electrode 48*a*. An end portion 53 of the motion transmitting member is coupled to the aerosolizing element 16.

An oscillating electric current applied to the electrodes 48*a*, 48*b* induces vibratory motion of the piezoelectric element 50, which in turn induces vibratory motion of the motion transmitting member 52 in the directions indicated by double-headed arrow 55. The motion transmitting member 52 transmits the vibratory motion to the aerosolizing element 16 for aerosolizing an agent therein. In particular embodiments, the actuator 18 generates vibrations in the range of about 20 to 200 Hz. Other types of actuators, such as a solenoid or a linear electric motor (e.g., a voice coil, such as used in a loudspeaker), also can be used to induce vibration of the aerosolizing element.

As discussed above, the actuator 18 is mounted within the air manifold 36, which directs compressed gas (e.g., compressed air) to flow over the actuator 18 and carry away heat generated during operation. The manifold 36 is formed with a flow channel 38 substantially surrounding the actuator 18 and an opening 42 that is connected to a compressed air conduit 44. The air conduit 44 receives compressed air from a compressed air source, such as the illustrated air pump 46. The manifold 36 is also formed with one or more apertures 40, which direct air in the flow channel 38 to flow through the aerosolizing element 16 in the direction of arrows 41. Air flowing through the aerosolizing element 16 entrains aerosol droplets expelled from the aerosolizing element and assists in the delivery of the droplets to the patient.

In lieu of or in addition to the air manifold 36, a heat sink 124 (FIGS. 21A and 21B) can be mounted to the actuator 18 to facilitate the dissipation of heat generated during operation. As shown in FIGS. 21A and 21B, the heat sink 124 includes a plurality of angularly spaced radial fins 126 extending longitudinally from a base 128 mounted to and in thermal contact with the actuator 18. In particular embodiments, the air manifold 36 can be sized to accommodate the actuator 18 and the heat sink 124. In other embodiments, the actuator 18 and optionally the heat sink 124 can be mounted in the housing 12 without the air manifold 36. In the latter embodiments, air from the air pump 46 can be ducted directly to the aerosolizing element 16 to assist in the delivery of aerosolized agent to the patient.

As shown in FIGS. 1A and 1B, the device 10 can include a wearable or body mountable pack or case 54 that houses the air pump 46 (e.g., a diaphragm air pump), an air filter 56, and one or more batteries 58 for powering the device. The pack 54 can be, for example, a waist pack ("fanny pack") that can be worn around the waist of a user or a shoulder or back pack that can be worn over one or both shoulders of a user. The pack 54 also can include a controller 66, a charging jack 62 for recharging the batteries 58, and an on/off power switch 61. The charging jack 62 can be connected to an external power supply (not shown) in a conventional manner to recharge the batteries 58 or to provide power to operate the device without use of the batteries. The pack 54 can be coupled to the housing 12 via a flexible umbilical 60 that contains the air conduit 44 and wiring connecting the controller 66 to the actuator 18 and a trigger switch 64 on the housing. By housing the pump 46, the batteries 58, and the controller 66 in the pack 54, the overall weight of the housing 12 can be reduced for easier handling. In an alternative embodiment, one or more of these components can be housed in the handle portion 14 or in another portion of the housing.

Although not shown in the illustrated embodiment, a compressed air receiver or reservoir can be housed in the handle portion 14 or the pack 54. The air reservoir can have an inlet that receives compressed air from the air pump 46 via a first conduit and an outlet that supplies a charge of compressed air to the air manifold 36 via another conduit. In another embodiment, the handle portion 14 can be equipped with a hand pump operable to charge the air receiver, such as disclosed in co-pending U.S. application Ser. No. 10/471,620 (U.S. Patent Application Publication No. US-2004-0134494), which is incorporated herein by reference. The device 10 also can be equipped with a hand-crank dynamo operable to recharge the batteries 58, such as disclosed in the '620 application.

The aerosol delivery device 10 can be operated in a continuous or automatic dose timing mode. A selector switch (not shown) can be provided on the handle portion 14 or on the pack 54 for manually setting the device to operate in either mode. In the continuous mode, a user depresses the trigger switch 64 on the handle portion 14, which sends a signal to the controller 66. The controller 66 sends a signal to the air pump 46 and the actuator 18 to begin operation. The aerosolizing element 16 converts an agent drawn from the vial 22 into droplets of a very small size (e.g., in a range of about 1 to 10 micrometers, although the size of the droplets can vary depending on the application). After administering a dose, the user depresses the trigger switch 64 again to turn off the actuator and the air pump.

In the automatic dose timing mode, the user first sets a timer switch (e.g., a rotary switch) (not shown) operatively connected to the controller at a desired setting corresponding to a predetermined aerosolization period (e.g., 15, 20, 30, or 60 seconds). In alternative embodiments, the device 10 can include a keypad or another type of input device to allow the user to set the desired time of application. To initiate administration of a dose, the user depresses the trigger switch 64, which activates the pump 46 to supply air to the manifold 36. After a predetermined period of time (e.g., 0.5 seconds), the actuator 18 is activated to aerosolize the agent in the aerosolizing element 16. At the end of the aerosolization period, the actuator 18 is automatically turned off, after which the aerosolization element can be purged with compressed air from the pump 46 for a predetermined period of time (e.g., 5 seconds) or until the switch 64 is depressed.

FIG. 2 shows another embodiment of the aerosol delivery device 10 that is similar to the embodiment shown in FIGS. 1A and 1B, except that it includes a hinged front portion 68 that is coupled to the housing 12 by a pivot pin 69. The front portion 68 is pivotable about the pin 69 (in the directions indicated by double-headed arrow 70) between an open position for removing or replacing the aerosolizing element 16 (as shown in FIG. 2) and a closed position in which the aerosolizing element 16 is held firmly in place between the front portion 68 and the adjacent surface of the housing 12. The housing 12 may be provided with a latch 71 that engages a corresponding surface of the front portion 68 to releasably retain the front portion 68 in the closed position. A latch button 72 on the latch 71 extends upwardly through the top of the housing 12. Depressing the latch button 72 releases the latch 71 from engagement with the front portion 68 so that it can be moved to the open position shown in FIG. 2. Various other latch or lock mechanisms can be implemented to releasably retain the front portion 68 in the closed position.

Figure 3A:
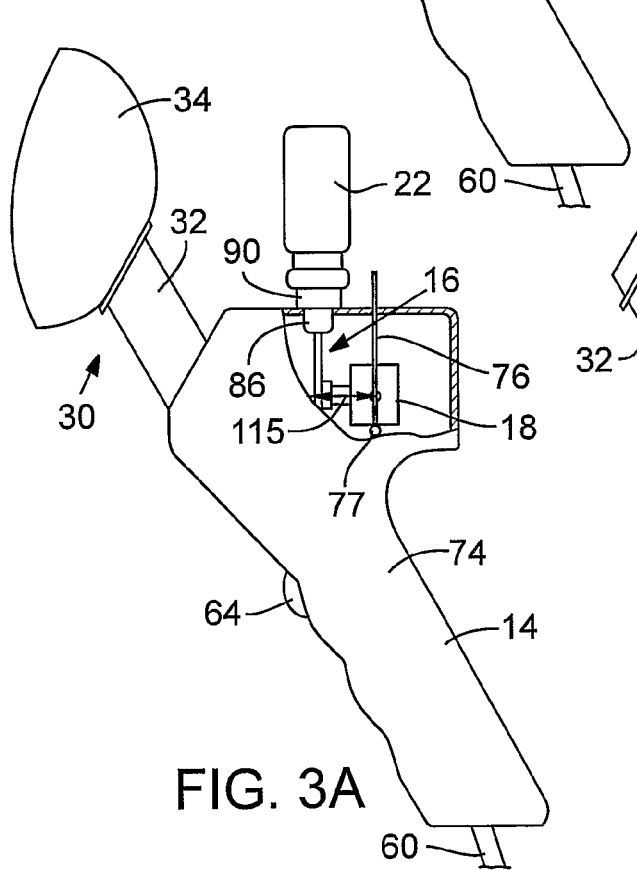
FIGS. 3A and 3B are side views, shown partially in section, of an aerosol delivery device, according to yet another embodiment.
Figure 3B:
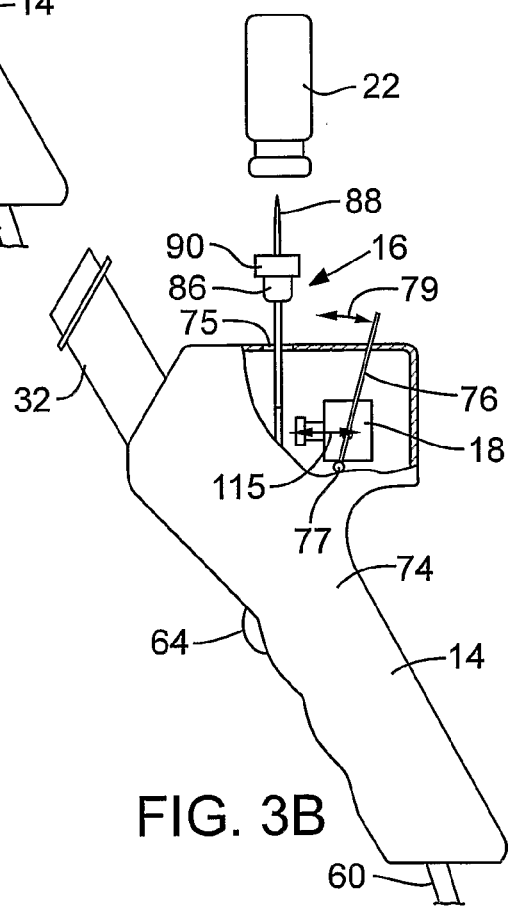

FIGS. 3A and 3B show another embodiment of the aerosol delivery device 10 that is similar in most respects to the embodiment shown in FIGS. 1A and 1B. The embodiment of FIGS. 3A and 3B includes a housing 74 formed with an upper opening 75 (FIG. 3B) that is sized to receive the aerosolizing element 16. As shown in FIG. 3A, when inserted into the opening 75, the aerosolizing element 16 is supported in an upright position by the top wall of the housing 74. The actuator 18 in this configuration is coupled to a movable lever 76 that is operable to move the actuator 18 between a first, operating position in which the actuator engages the aerosolizing element 16 (FIG. 3A) and second position in which the actuator is spaced from the aerosolizing element (FIG. 3B). The lower end of the lever 76 is pivotally mounted inside the housing 74 at a pivot pin 77 to permit pivoting of the lever in the directions indicated by double headed arrow 79. The upper end portion of the lever 76 extends through the top wall of the housing 74 for manipulation by a user. The actuator 18 is coupled to the lever 76 by a pinned connection or equivalent mechanism such that the actuator 18 is displaced along a substantially straight path (in the directions indicated by doubled-headed arrow 115) upon pivoting movement of the lever.

Prior to loading the aerosolizing element 16 into the housing, the lever 76 is moved toward the rear of the housing to the position depicted in FIG. 3B. After insertion of the aerosolizing element, the lever is moved toward the front of the housing to move the actuator 18 to the operating position depicted in FIG. 3A.

Turning now to FIGS. 4A and 4B, the aerosolizing element 16 will now be described. The aerosolizing element 16 has a body 78 that includes a front portion 80, a rear portion 82, a chamber 84 cooperatively formed between the front portion 80 and the rear portion 82, and an integral reservoir 86 formed at the upper end portion of the aerosolizing element and in fluid communication with the inlet of the chamber 84. A piercing prong, or needle, 88 extends upwardly from a vial mount 90 situated on top of the reservoir 86. The prong 88 has a pointed upper end that is used to puncture a puncturable septum 92 incorporated or connected to the opening of the vial 22. The septum 92 can be made of an elastomeric material (e.g., rubber) or any of various other suitable materials. The prong 88 also functions to hold the vial 22 in an inverted position on top of the vial mount 90. While the illustrated prong 88 is a small cylindrical tube, other shaped tubes, including square, triangle, or rectangle, also can be used.

The prong 88 is formed with a first flow passageway 94 extending between the upper end of the prong and the reservoir 86 to allow agent in the vial 22 to flow into the reservoir. A second flow passageway 96 in the prong 88 extends between the upper end of the prong and an air inlet, or opening, 98 formed in the vial mount 90. The opening 98 can be fitted with a porous (air permeable) plug 100 (FIG. 4B). The second flow passageway 96 allows atmospheric air to be drawn into the vial 22 to replace agent that is extracted from the vial. The reservoir 86 also can be provided with an air outlet, or opening, 102 (FIG. 4A) fitted with a porous plug (not shown) to allow for venting of air in the reservoir. The porous plugs in openings 98 and 102 are made of a material that is permeable to air but inhibits leakage of the agent due to surface tension.

The front portion 80 of the aerosolizing element 16 defines an orifice surface 104 that is formed with a plurality of orifices 110. The rear portion 82 defines a movable element 106 opposite the orifices 110 that is coupled to the end portion 53 of the actuator 18. The movable element 106 is movable or deformable to increase pressure in the chamber 84 in response to the force applied by the actuator 18. In the illustrated embodiment, for example, the movable element 106 comprises a flexible diaphragm that alternately flexes inwardly and outwardly in response to movement of the actuator. In operation, rapid motion of the actuator 18 pushes the diaphragm inwardly and toward the orifices 110, increasing pressure in the chamber 84 and expelling agent outwardly through the orifices 110 to form aerosol droplets 108. Movement of the actuator 18 in the opposite direction causes the diaphragm to flex outwardly and away from the orifices, thereby decreasing the pressure in the chamber 84 and drawing agent into the region of the chamber behind the orifices for the next cycle. In alternative embodiments, the movable portion need not be flexible or deformable but is otherwise configured to move toward and away from the front portion 80 in response to movement of the actuator 18.

As shown in FIG. 4A, the aerosolizing element 16 can be formed with one or more air flow apertures, or openings, 112 extending through a peripheral portion of the element adjacent the orifice surface 104. The openings 112 are in fluid communication with the apertures 40 of the air manifold 36 (FIG. 1B) at the rear surface of the element 16 so that air from the apertures 40 can flow through the openings 112 and entrain droplets 108 expelled by the orifices 110 for delivery to the patient.

The orifices 110 typically are about 5 micrometers in diameter, although the size of the orifices can vary depending on the desired size of the droplets 108. The front and rear portions 80, 82 can be made from any of various suitable materials, such as plastic, using conventional manufacturing techniques (e.g., molding). The orifices 110 can be formed directly in the front portion 80 using conventional micromachining techniques, such as laser drilling, electroforming, or chemical etching. As depicted in FIG. 4B, the rear portion 82 can be of a unitary construction having a substantially constant thickness. In other embodiments, the rear portion can have a relatively thinner section opposite the orifices 110 that defines the movable element 106. In another embodiment (e.g., the aerosolizing element 800 shown in FIGS. 22A-22C, which is described below), the movable element can be a separate element bounding the chamber opposite the orifices. In the latter embodiment, the rear portion 82 can be formed with an opening to receive the actuator 18 for coupling to the movable element.

Preferably, the aerosolizing element 16 is disposable. If the device is used where disposal costs are not prohibitive (e.g., in a modern hospital), the aerosolizing element (and the mask 34) can be disposed of each time a dose is administered to a patient. However, if the device is used in a high workload application, such as a mass vaccination campaign, disposal costs may be a concern. In such cases, the aerosolizing element can be used to administer doses to multiple patients, but typically would be disposed of after a session of administering multiple doses to prevent the growth of bacteria or other contaminants. Notably, the aerosolizing element 16 inhibits contact of the agent with the actuator 18 and other re-useable components of the device 10. Consequently, substantially less time is required for cleaning and maintenance of the device compared to conventional nebulizers.

Figure 5:
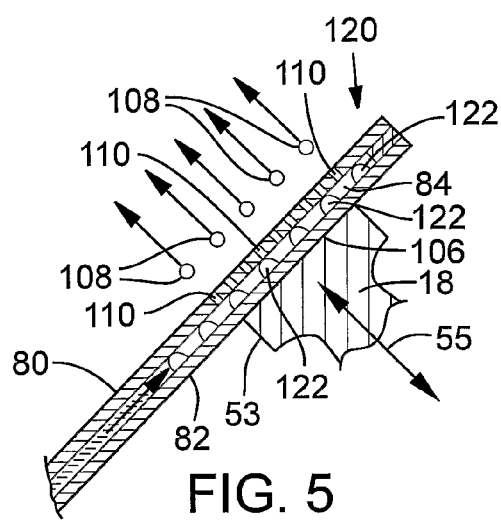
FIG. 5 is cross-sectional view of an embodiment of a capillary feed aerosolization element for an aerosol delivery device.

FIG. 5 shows an aerosolizing element 120, according to another embodiment, that can be used in any of the aerosol delivery devices described herein. The aerosolizing element 120 is similar to the aerosolizing element 16, except that agent is drawn upwardly to the area of the chamber 84 behind the orifices 110 by capillary action. The aerosolizing element 120 can be provided with a piercing prong 88 for drawing agent upwardly from a vial 22 (not shown in FIG. 5). Alternatively, rather than drawing agent from a vial, the aerosolizing element 120 can include an integral reservoir sized to receive a predetermined quantity of an agent sufficient for supplying a single dose or multiple doses.

The thickness of the chamber 84 (the distance measured between the opposed internal surfaces of the front and rear portions 80, 82) is selected to maintain an adequate flow of agent via capillary action without inducing a pressure loss that exceeds the capillary head. As shown, the aerosolizing element 120 can include one or more spaced apart dimples, or projections, 122 disposed in the chamber 84. The projections 122 maintain a minimum spacing in the chamber 84 between the movable portion 106 and the front portion 80 of the element so as to maintain adequate capillary head without undue pressure loss.

Figure 6:
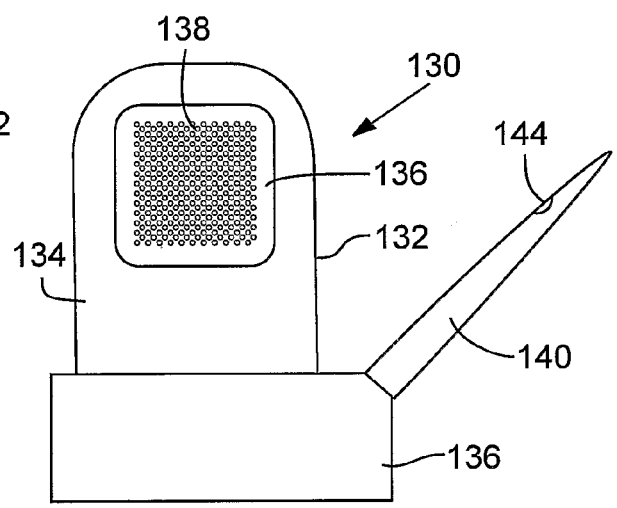
FIG. 6 is a front elevation view of another embodiment of an aerosolization element for an aerosol delivery device.
Figure 7A:
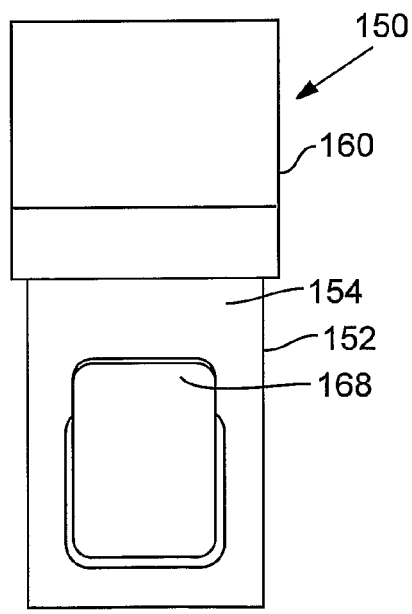
FIGS. 7A and 7B are front elevation and cross-sectional views, respectively, of another embodiment of an aerosolization element for an aerosol delivery device.
Figure 7B:
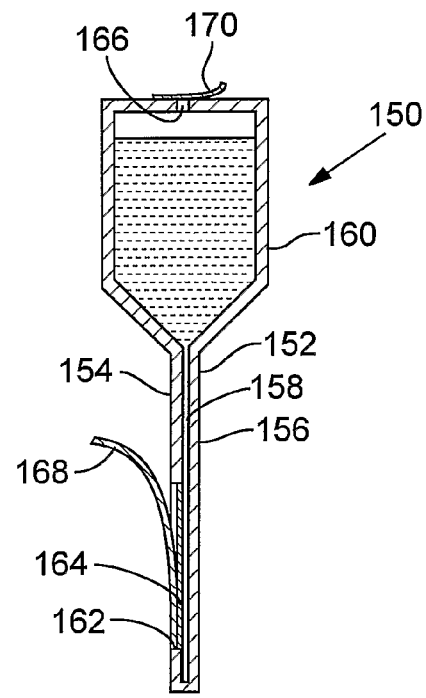

FIG. 6 shows an aerosolizing element 130, according to another embodiment, that can be used in any of the aerosol delivery devices described herein. The aerosolizing element 130 has a body 132 that includes a first portion 134 and a second, deformable portion 136 that serves as a reservoir for an agent to be aerosolized. The first portion 134 has a construction that is similar to the aerosolizing element 16 in that it includes an internal chamber (not shown) for receiving an agent to be aerosolized, an orifice area 136 defining a plurality of orifices 138, and a movable portion (not shown) bounding the chamber opposite the orifices 138 for forcing agent through the orifices 138. The deformable portion 136 of the aerosolizing element 130 is made of a flexible, resilient material, such as rubber or another suitable elastomer. A piercing prong 140 extends from the deformable portion 136 for insertion into a vial 22. The piercing prong 140 is formed with an opening 144 to receive agent from the vial. The deformable portion 136 functions in a manner similar to the squeeze bulb on a conventional eyedropper. Prior to inserting the prong 140 into a vial, the user squeezes the deformable portion 136. After insertion, finger pressure is removed from the deformable portion 136, allowing it to return to its normal shape and thereby drawing agent from the vial via the prong 140. The agent in the deformable portion 136 can be fed into the chamber of the first portion 134 via gravity or capillary action, as described above in connection with the embodiments shown in FIGS. 4A, 4B, and 5.

FIGS. 7A and 7B show an aerosolizing element 150, according to another embodiment, that can be used in any of the aerosol delivery devices described herein. The aerosolizing element 150 has a body 152 that includes a front portion 154, a rear portion 156, a chamber 158 cooperatively formed between the front portion 154 and the rear portion 156, and an enlarged reservoir 160 formed at the upper end portion of the element and in fluid communication with the inlet of the chamber 158. The reservoir 160 can be sized to hold a predetermined volume of agent sufficient to deliver a single dose or multiple doses. The reservoir 160 desirably is provided with a venting port 166 to expose the interior of the reservoir to atmosphere when agent is drawn from the reservoir into the chamber 158. Although not shown in FIGS. 7A and 7B, a removable piercing prong can be inserted into the venting port 166 for supplying agent to the reservoir 160 from a vial 22. Additionally, the reservoir 60 can be filled via port 166 using a needle and syringe or equivalent device. The agent can be fed from the reservoir 160 into the chamber 158 via gravity or capillary action.

The front portion 154 is formed with an opening 162 (FIG. 7B) in which there is fitted an orifice plate 164 having multiple orifices for expelling droplets of agent. In one implementation, the aerosolizing element 150 is filled with a predetermined volume of agent and sealed by a pharmaceutical manufacturer or pharmacy. In this regard, a removable sealing tape 168 can be placed over the orifice plate 164 to prevent leakage of agent and the ingress of foreign matter and other desired material into element prior to use. Likewise, a removable sealing tape 170, a removable tab or other closure can be used to close the venting port 166. The sealing tapes 168 and 170 are then removed by the user prior to administering the agent.

FIGS. 8A-8C show an aerosolizing element 180, according to yet another embodiment, that can be used in any of the aerosol delivery devices described herein. The aerosolizing element 180 differs from the previously described embodiments in that it can be used to store and mix two different liquid components. As shown, the aerosolizing element 180 has a body 182 that includes a front portion 184, a rear portion 186, a chamber 188 cooperatively formed between the front portion 184 and the rear portion 186, a first reservoir 190 in fluid communication with the inlet of the chamber 188, and a second reservoir 192 defined at the upper end portion of the aerosolizing element. An orifice plate 164 is disposed in an opening formed in the front portion 184.

As shown in FIG. 8B, the chamber 188 and the first reservoir 190 are filled with a first liquid and the second reservoir 192 is filled with a second liquid. A plug, or separation element, 194 is disposed in the aerosolizing element 180 between the first and second reservoirs to keep the liquids separated from each other prior to use. The second reservoir 192 has an open top that is fitted with a plug 196. A removable, annular ring 198 is disposed around the plug 196 and seated against the open end of the second reservoir 192. The plug 196 is formed with an annular flange portion 197 that overlaps the ring 198. The ring 198 prevents inadvertent or premature mixing of the first and second liquids by resisting movement of the plug 196 into the second reservoir 192.

Figures 8A, 8B, 8C:
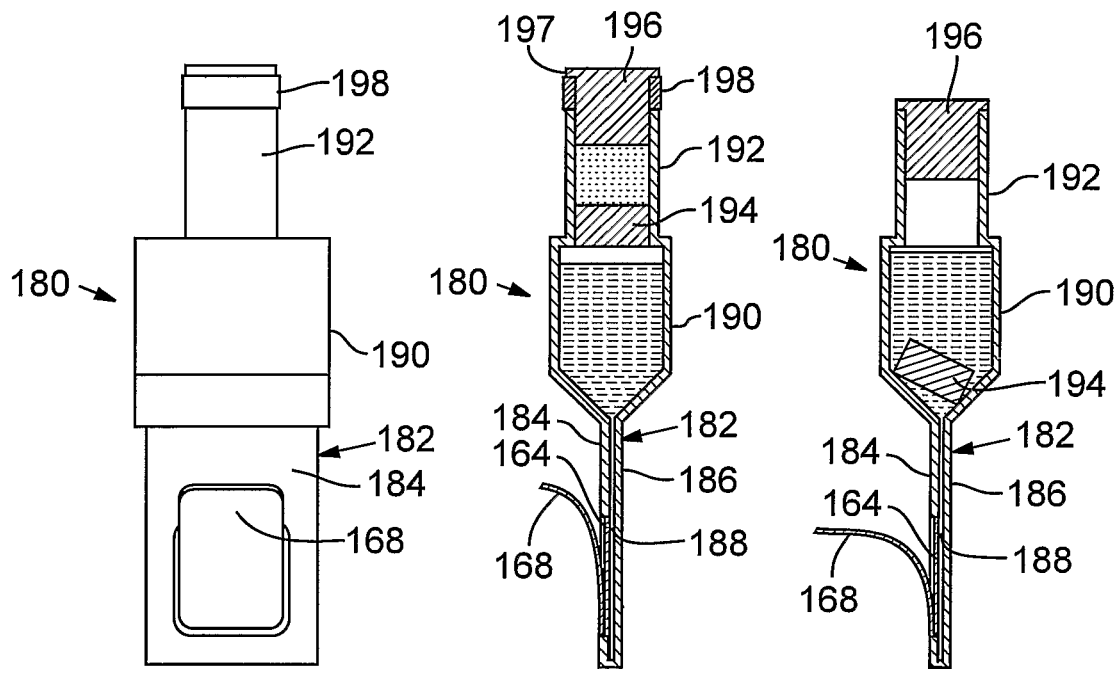
FIGS. 8A and 8B are front elevation and cross-sectional views, respectively, of another embodiment of an aerosolization element that is used to store and mix two liquid components.
FIG. 8C is a cross-sectional view similar to FIG. 8B, showing the aerosolization element after the liquid components are mixed together to form an agent to be aerosolized.

To reconstitute the first and second liquids at the time of use, the user removes the ring 198 and pushes down on the plug 196 to pressurize the second reservoir 192. Due to the incompressibility of the liquid, the liquid forces the plug 194 into the wider area of the first reservoir 190, thereby allowing the liquid in the second reservoir to mix with the liquid in the first reservoir (as shown in FIG. 8C). In use, the agent can be fed from the reservoir 190 into the chamber 188 via gravity or capillary action.

Figures 9A, 9B:
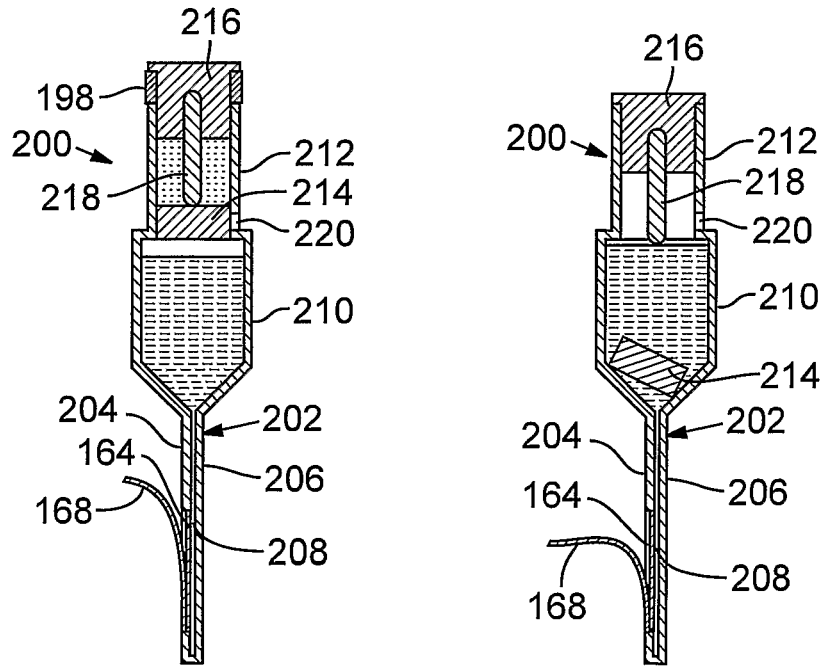
FIG. 9A is a cross-sectional view of another embodiment of an aerosolization element that contains a liquid component separated from a dry component
FIG. 9B is a cross-sectional view similar to FIG. 9A, showing the aerosolization element after the liquid component and dry component are mixed together to form an agent to be aerosolized.

FIGS. 9A and 9B show an aerosolizing element 200, according to yet another embodiment, that can be used in any of the aerosol delivery devices described herein. The aerosolizing element 200 differs from the previously described embodiments in that it can be used to store and mix a liquid component and a dry component (e.g., a solid or powdered component). As shown, the aerosolizing element 200 has a body 202 that includes a front portion 204, a rear portion 206, a chamber 208 cooperatively formed between the front portion 204 and the rear portion 206, a first reservoir 210 in fluid communication with the inlet of the chamber 208, and a second reservoir 212 defined at the upper end portion of the aerosolizing element. An orifice plate 164 is disposed in an opening formed in the front portion 204.

As shown in FIG. 9A, the chamber 208 and the first reservoir 210 are filled with a liquid (e.g., a diluent for a dry component) and the second reservoir 212 is filled with a powder (e.g., lyophilate) or another type of dry component A plug 214 is disposed in the aerosolizing element 200 between the first and second reservoirs to keep the dry component separated from the liquid component prior to use. The second reservoir 212 has an open top that is fitted with a plug 216. A rigid push rod 218 (e.g., a glass rod) extends from the plug 216 and contacts the plug 214 (FIG. 9A). The body 202 can be formed with a venting port 220 between the first and second reservoirs 210 and 212 adjacent the plug 214. As shown in FIG. 9A, the plug 214 covers the port 220 to prevent leakage prior to use.

To reconstitute the liquid and dry components at the time of use, the user removes the ring 198 and pushes down on the plug 216. Movement of the plug 216 and the push rod 218 forces the plug 214 into the wider area of the first reservoir 210, thereby allowing the dry component in the second reservoir to mix with the liquid in the first reservoir and form an agent for administering to a patient (as shown in FIG. 9B). Displacement of the plug 214 also exposes the first reservoir 210 to atmospheric pressure via the venting port 220 to facilitate the flow of agent into the chamber 208. In use, the agent can be fed from the reservoir 210 into the chamber 208 via gravity or capillary action.

FIGS. 10A-10C show an aerosolizing element 250, according to another embodiment, that can be used in any of the aerosol delivery devices described herein. The aerosolizing element 250 has a body 252 that includes a front portion 254, a rear portion 256, a chamber 258 cooperatively formed between the front portion 254 and the rear portion 256, and an integral reservoir 260 formed at the upper end portion of the aerosolizing element and in fluid communication with the inlet of the chamber 258. The reservoir 260 desirably is provided with a venting port 266 to expose the interior of the reservoir to atmosphere pressure when agent is drawn from the reservoir into the chamber 258. In use, the agent can be fed from the reservoir 260 into the chamber 258 via gravity or capillary action.

The front portion 254 is formed with an opening in which there is fitted an orifice plate 164 for expelling droplets of agent. The body 252 further includes peripheral portions 268, 270 on opposite sides of the chamber 258 (FIG. 10A). Formed in the peripheral portions 268, 270 are respective air flow passageways 272 (FIGS. 10B and 10C). As best shown in FIG. 10C, each passageway 272 extends from an inlet 274 formed in the rear portion 256 to one or more outlets 276 formed in the front portion 254 at locations offset from the inlet 274. When the aerosolizing element 250 is placed in the housing of an aerosol delivery device (e.g., the device 10 shown in FIGS. 1A and 1B), the inlets 274 are positioned to receive compressed air from the air manifold 36. Air flows into the inlets 274, through the passageways 272 and exits the outlets 276 (as indicated by arrows 278) to entrain droplets expelled by the orifice plate 164. Because the outlets 276 are offset from the inlet 274, there is less likelihood that expired particles from the patient can travel through the passageways and contact the actuator 18 or other reusable portions of the system.

FIGS. 22A-22C show an aerosolizing element 800, according to another embodiment, that can be used in any of the aerosol delivery devices described herein. The aerosolizing element 800 has a body 802 that includes a front portion 804, a rear portion 806, and a reservoir 810 formed at the upper end portion of the aerosolizing element. The reservoir 810 desirably is provided with a venting port 812.

Disposed between the front and rear portions 804, 806 is an orifice plate 814 (e.g., an electroformed mesh plate) and a flexible spacer element 816. A chamber 808 for receiving agent from the reservoir 810 is defined between the orifice plate 814 and the spacer element 816. The orifice plate 814 is formed with a plurality of orifices 818 that are aligned with an opening 820 in the front portion 804. The spacer element 816 is formed with a plurality of projections 824 that maintain a minimum spacing in the chamber 808 between the orifice plate 814 and the spacer element 816. Although not required, the orifice plate 814 and the spacer element 816 can be held together by a piece of adhesive tape 826 placed over the orifice plate and secured to the lower end portion of the spacer element for ease of assembly. The tape 826 is formed with an opening 828 aligned with the opening 820 in the front portion 804. The rear portion 806 is formed with an opening 836 that is sized to receive the front end portion 53 of the actuator 18 (FIG. 4B). A piece of double-sided tape 840 can be used to secure the end portion 53 of the actuator 18 to the spacer element 816. A suitable sealant (e.g., silicone) can be used to secure the tape 826 to the inside surface 832 of the front portion 804 and to secure the spacer element 816 to the inside surface 834 of the rear portion 806.

In particular embodiments, the orifice plate 814 comprises a thin metal foil (e.g., nickel, aluminum, gold, or another suitable metal) having a thickness of about 0.05 mm. Other suitable materials, such as ceramics or composite materials, also can be used to form the orifice plate 814. The orifices 818 can be formed using conventional micro-machining techniques, such as laser drilling, electroforming, and chemical etching. The spacer element 816 comprises a thin flexible plastic having a thickness of about 0.1 mm. The projections 824 on the spacer element 818 have a height of about 0.1 mm. Of course, these specific dimensions (as well as other dimensions provided in the present specification) and materials are given to illustrate the invention and not to limit it. The dimensions and materials provided herein can be modified as needed in different applications or situations.

The spacer element 816 serves as a flexible diaphragm for expelling agent through the orifice plate 814. In use, the end portion 53 of the actuator 53 extends through the opening 836 and bears against the spacer element 816. Vibration of the actuator 18 is transmitted to the spacer element 816, causing it to flex toward and away from the orifice plate 814, alternately forcing agent in the chamber 808 through the orifices 818 and drawing agent into the chamber 808 from the reservoir 810.

FIG. 11 shows an extension portion 300 of a patient interface that can be used with the aerosol delivery device 10 (or other delivery devices), according to another embodiment. The extension portion 300 is similar to the extension portion 32 shown in FIGS. 1A and 1B, except that the extension portion 300 includes one or more openings, or vents, 302 proximate the housing 12. A disposable mask 34 (not shown in FIG. 11) can be coupled to the end of the extension portion 300 in the manner shown in FIGS. 1A and 1B. The openings 302 allow inspiratory air to be drawn into the extension portion 300, as indicated by arrows 304, so as to allow the patient to breathe normally during the administration of an agent. As outside air enters the extension portion, the air entrains aerosol droplets expelled by the aerosolizing element 16 to assist in the delivery of droplets to the patient.

Figure 12:
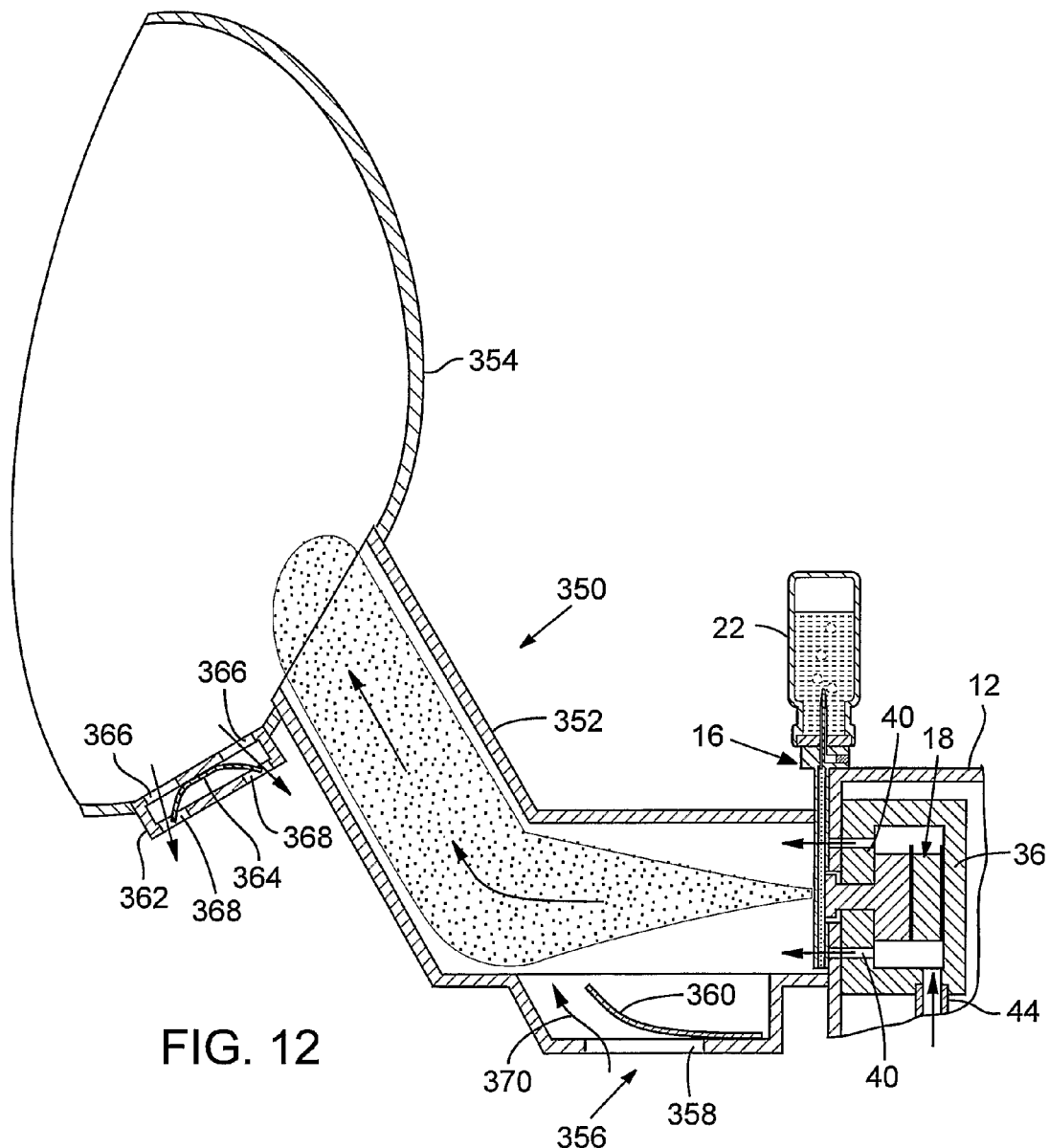
FIG. 12 is an enlarged cross-sectional view of another embodiment of a patient interface shown being used with the aerosol delivery device of FIGS. 1A and 1B.

FIG. 12 shows a patient interface 350 that can be used with the aerosol delivery device 10 (or other delivery devices), according to another embodiment. The patient interface 350 includes an extension portion 352 extending from the housing 12 and a disposable mask 354 coupled to the end of the extension portion 352. The extension portion 352 includes a one-way valve 356 that is operable to allow inspiratory air to flow into the extension portion and inhibit flow in the opposite direction to the surrounding environment. The illustrated valve 356 includes an opening 358 formed in the extension portion 352 and a flexible sealing member 360 secured at one end to the inside surface of the extension portion. The sealing member 360 can be made from a flexible and/or elastomeric material, such as rubber or any of various other suitable elastomers. In its normal, at rest position, the sealing member 360 covers the opening 358. During inhalation, the sealing member 360 opens to allow outside air to be drawn into the extension portion through the opening 358 (as indicated by arrow 370) to assist in the delivery of aerosol droplets to the patient. During exhalation, the sealing member 360 covers the opening 358 to prevent aerosolized agent in the extension portion from being released to the surrounding environment.

The mask 354 in this embodiment is made of a non-porous material (a material that does not allow passage of air) and includes a one-way valve 362 to allow for the release of expiratory flow. The valve 362 houses a flexible sealing member 364 that covers openings 366 in the mask in its normal, at rest position to prevent outside air from flowing into the mask. During exhalation, the sealing member 364 opens to allow expiratory air to flow through openings 366 and openings 368 to the environment.

Figure 13:
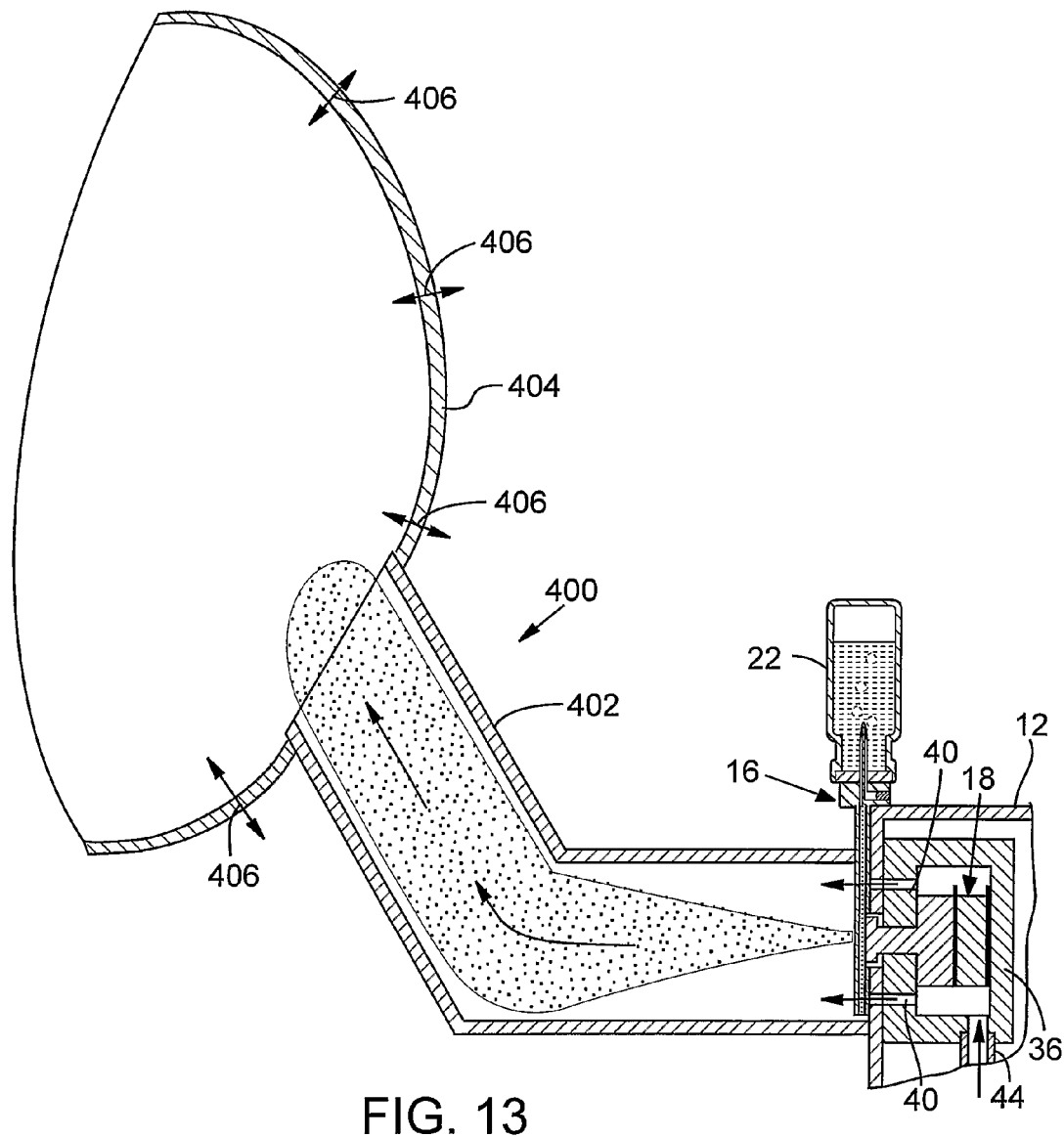
FIG. 13 is an enlarged cross-sectional view of another embodiment of a patient interface shown being used with the aerosol delivery device of FIGS. 1A and 1B.

FIG. 13 shows a patient interface 400 that can be used with the aerosol delivery device 10 (or other delivery devices), according to another embodiment. The patient interface 400 includes an extension portion 402 extending from the housing 12 and a disposable mask 404 coupled to the end of the extension portion 402. The mask 404 in this embodiment is made of a porous material that allows for the passage of air. The mask 404 can be manufactured from, for example, nonwoven polypropylene, such as used in conventional surgical or dust masks, or other suitable materials. Expiratory and inspiratory air can flow through the mask 404 (as indicated by double-headed arrows 406), but traps expired particulates (e.g., cough and sneeze particles) and aerosolized agent in the mask from being released to the environment. The extension portion 402 can include a one-way valve 356 (FIG. 12) to permit outside air be drawn into the flow path and assist in the delivery of aerosol droplets expelled by the aerosolizing element 16.

Figure 14:
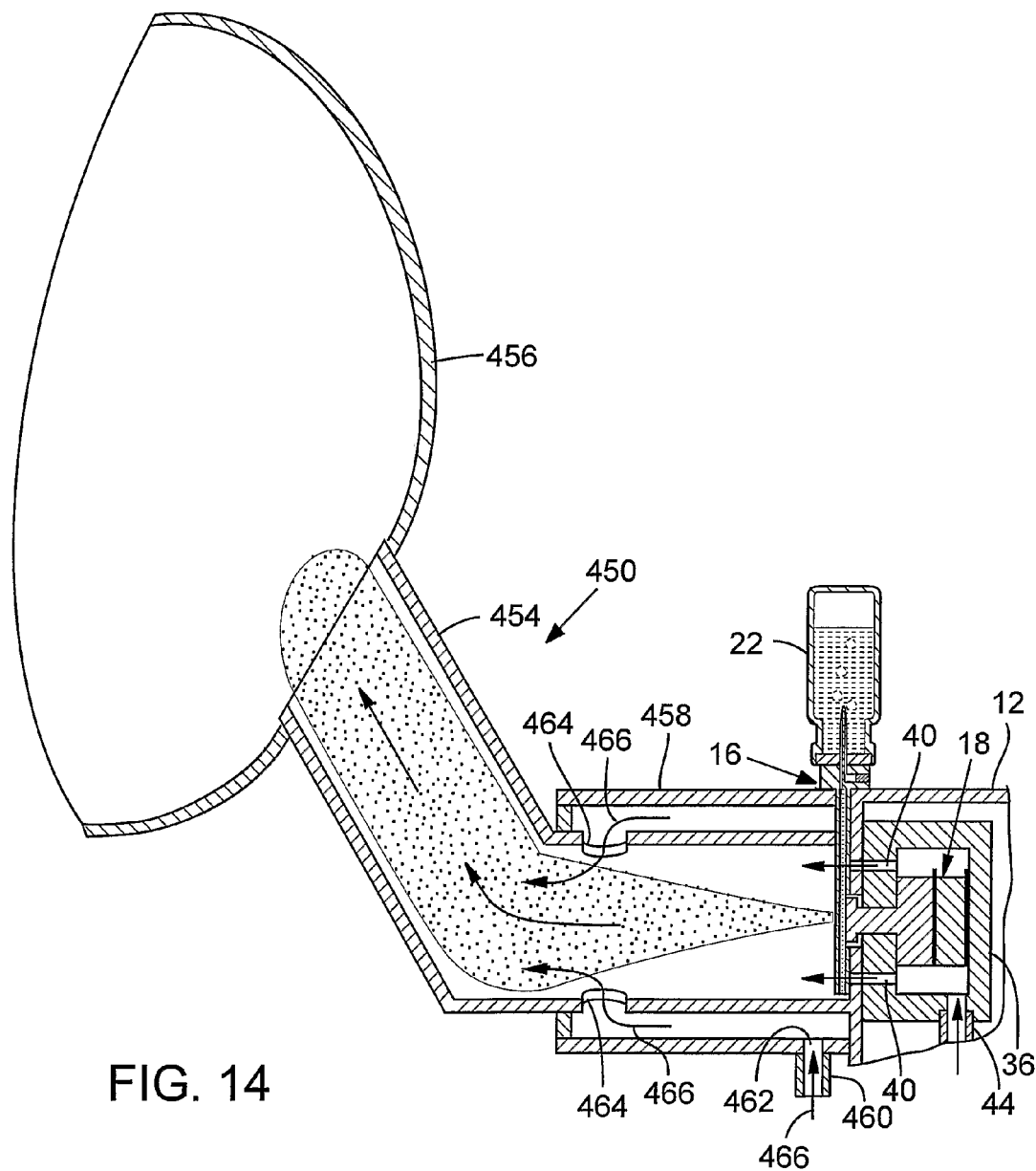
FIG. 14 is an enlarged cross-sectional view of another embodiment of a patient interface shown being used with the aerosol delivery device of FIGS. 1A and 1B.

FIG. 14 shows a patient interface 450 that can be used with the aerosol delivery device 10 (or other delivery devices), according to another embodiment. The patient interface 450 includes an extension portion 454 extending from the housing 12, a disposable mask 456 coupled to the end of the extension portion 454, and an air distribution plenum 458 co-axially disposed around the horizontal portion of the extension portion 454. A compressed air conduit 460 is connected to an air inlet 462 of the plenum 458 to deliver compressed air from the pump 46 (FIGS. 1A and 1B) (or another source of compressed air) to the plenum 458. The extension portion 454 is formed with one or more openings 464 inside of the plenum 458. In use, compressed air from the conduit 460 flows into the plenum 458, though openings 464 and into the extension portion 454 (in the direction of arrows 466). The air flow from the plenum further assists in the delivery of the aerosol droplets to the patient and reduces aerosol deposition on the internal surfaces of the extension portion by directing the aerosol droplets away from these surfaces.

Figure 15:
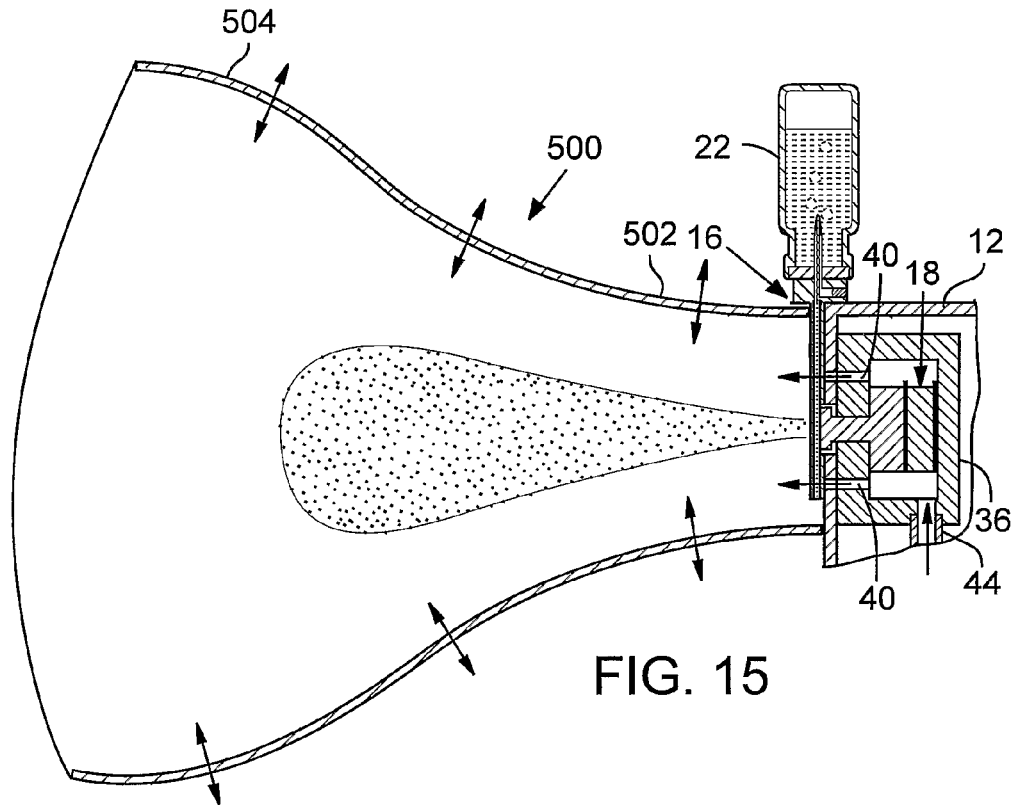
FIG. 15 is an enlarged cross-sectional view of another embodiment of a patient interface shown being used with the aerosol delivery device of FIGS. 1A and 1B.

FIG. 15 shows a patient interface 500 that can be used with the aerosol delivery device 10 (or other delivery devices), according to another embodiment. The patient interface 500 includes a first portion 502 extending from the housing 12 and a second, enlarged portion 504 sized to cover the nose and mouth of a patient. The patient interface 500 is made of a porous material to allow for the passage of expiratory and inspiratory air along the entire length of the interface. In the particular embodiments, the entire patient interface 500 is intended to be disposed of after each use to protect against patient-to-patient contamination.

Figure 16:
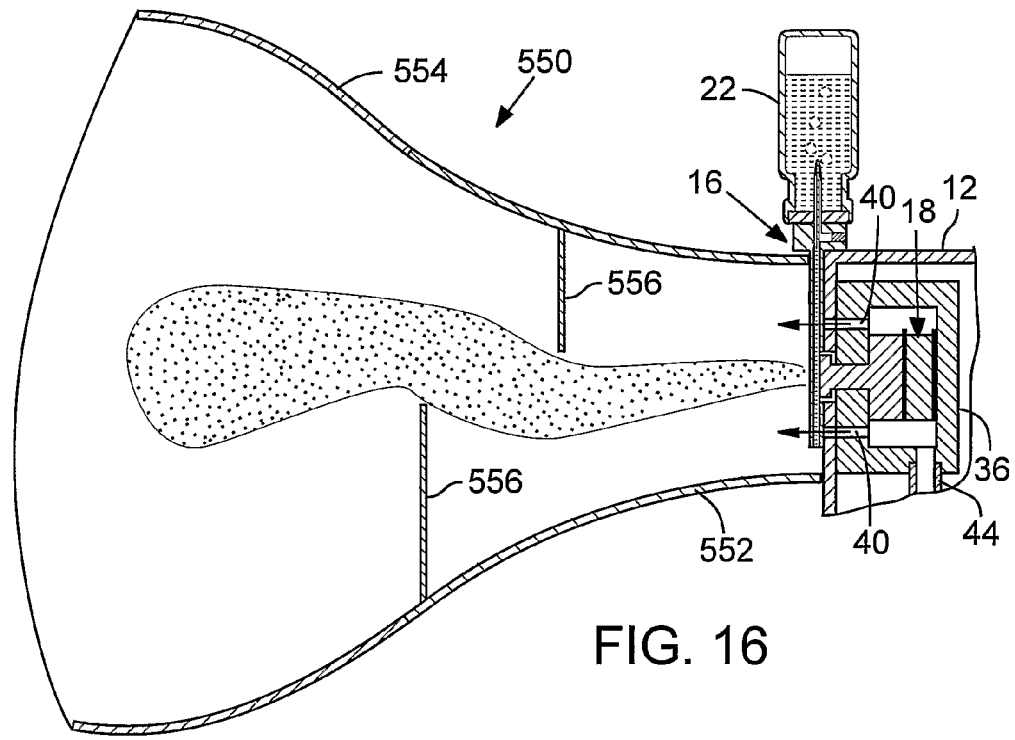
FIG. 16 is an enlarged cross-sectional view of a patient interface, according to another embodiment, shown being used with the aerosol delivery device of FIGS. 1A and 1B and having a plurality of internal baffles in the flow path to the patient.

FIG. 16 shows a patient interface 550 that can be used with the aerosol delivery device 10 (or other delivery devices), according to another embodiment. The patient interface 550 includes a first portion 552 extending from the housing 12 and a second, enlarged portion 554 sized to cover the nose and mouth of a patient. A plurality of baffles 556 are spaced along the length of the first portion 552 and extend into the flow path of aerosol droplets expelled from the aerosolizing element 16. The baffles 556 shield the aerosolizing element 16 and other re-usable components from expired particles (e.g., cough or sneeze particles) to protect against patient-to-patient contamination. In the illustrated embodiment, the first portion 552 is made of a non-porous material and the second portion 554 is made of a porous material. The first and second portions 552, 554 can be secured to each other using suitable techniques or mechanisms, such as adhesives or fasteners. Alternatively, the entire patient interface 550 can be made from single piece of porous material, similar to the patient interface 500 of FIG. 15, or from two separately formed pieces of porous material that are joined together to form the patient interface. The patient interface 550, like the patient interface 500, preferably is disposable.

Figure 17A:
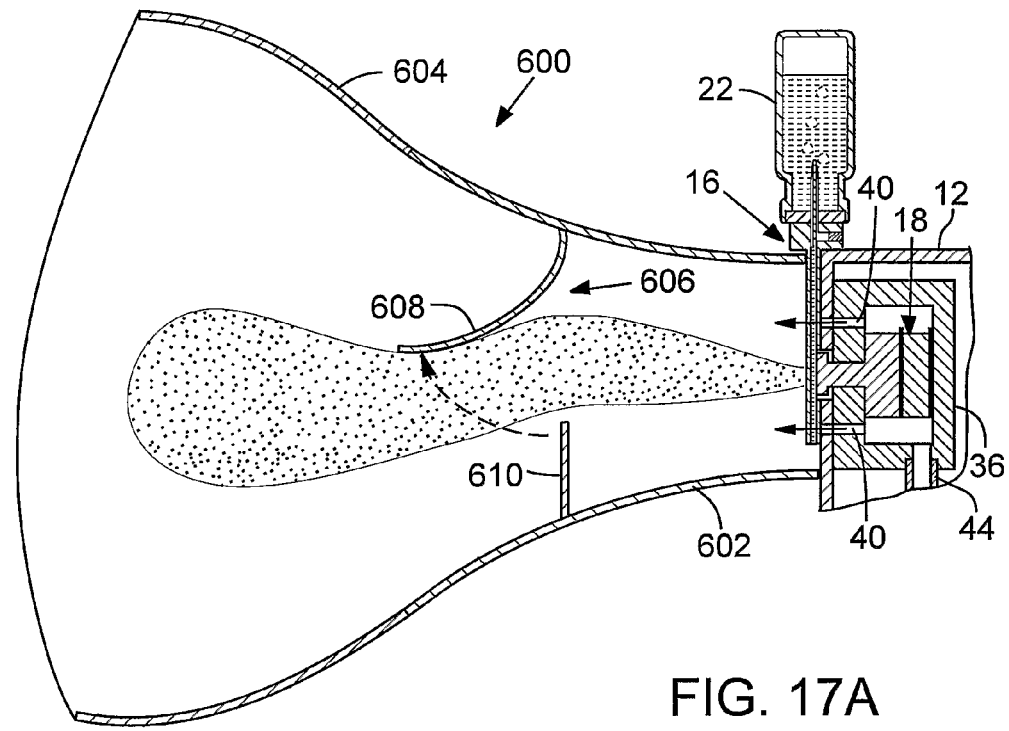
FIGS. 17A and 17B are enlarged cross-sectional views of patient interface, according to another embodiment, showing the operation of a one-way valve in the patient interface permitting flow from the aerosol delivery device to a patient, but inhibiting flow in the opposite direction.
Figure 17B:
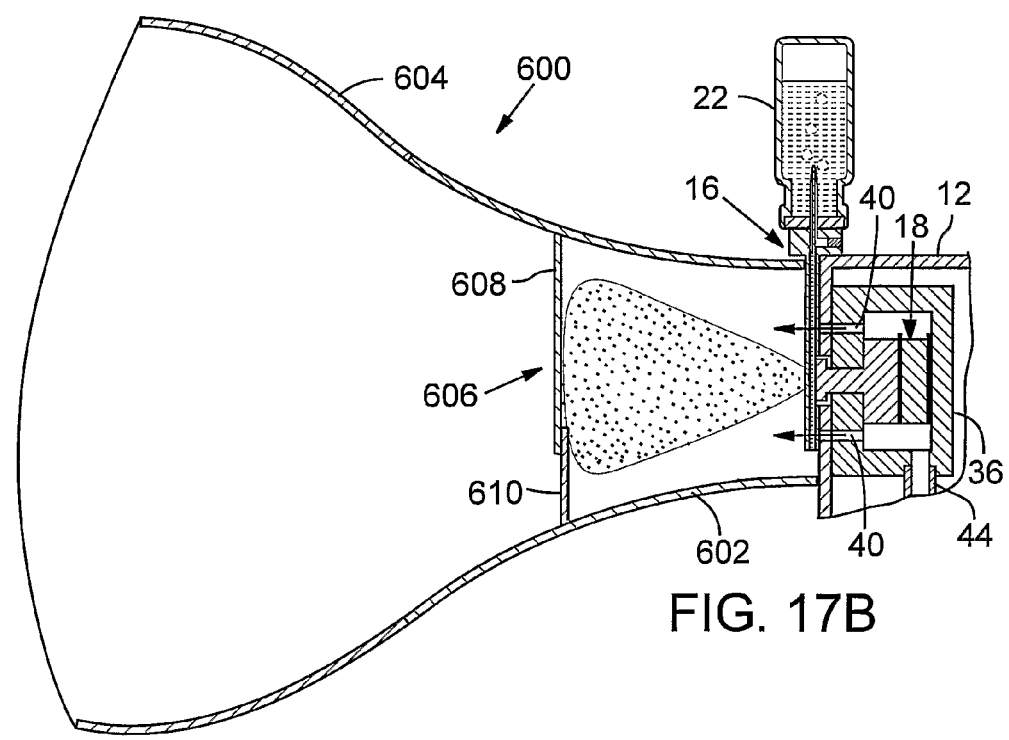

FIGS. 17A and 17B shows a patient interface 600, according to another embodiment, that includes a first portion 602 extending from the housing 12 and a second, enlarged portion 604 sized to cover the nose and mouth of a patient. The second portion 604 is made of a porous material while the first portion 602 may be made of a porous or non-porous material. The patient interface 600 is similar to the patient interface 550 of FIG. 16, except that the patient interface 600 includes a one-way valve 606 disposed in the first portion 602. The valve 606 is a flapper-type valve having a flexible sealing member 608 secured at one end to the inside surface of the first portion 602 and a non-movable valve seat 610 secured at one end to the inside surface of the first portion 602 opposite the sealing member 608.

In its normal, at rest position, the sealing member 608 contacts or partially overlaps the valve seat 610 to close the flow path from the aerosolizing element 16 to the patient (FIG. 17B). During inhalation, the sealing member 608 opens to allow aerosol droplets and air to flow to the patient (FIG. 17A). During exhalation, the valve closes (FIG. 17B) to protect the aerosolizing element 16 and other re-useable components against contamination from expired particles. In another embodiment, the patient interface 600 can include both the valve 606 and baffles 566 (FIG. 16) to further protect against contamination. The patient interface 600, like the patient interface 500, preferably is disposable.

Figure 18A:
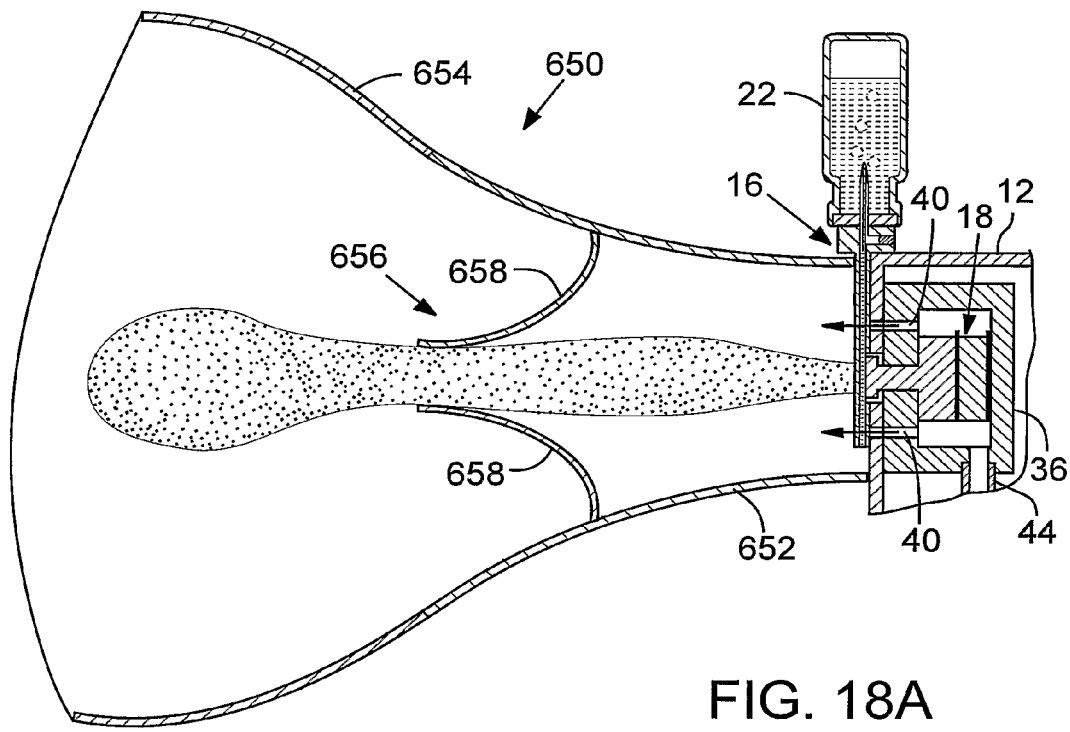
FIGS. 18A and 18B are enlarged cross-sectional views of a patient interface, according to another embodiment, showing the operation of a one-way, duckbill valve in the patient interface.
Figure 18B:
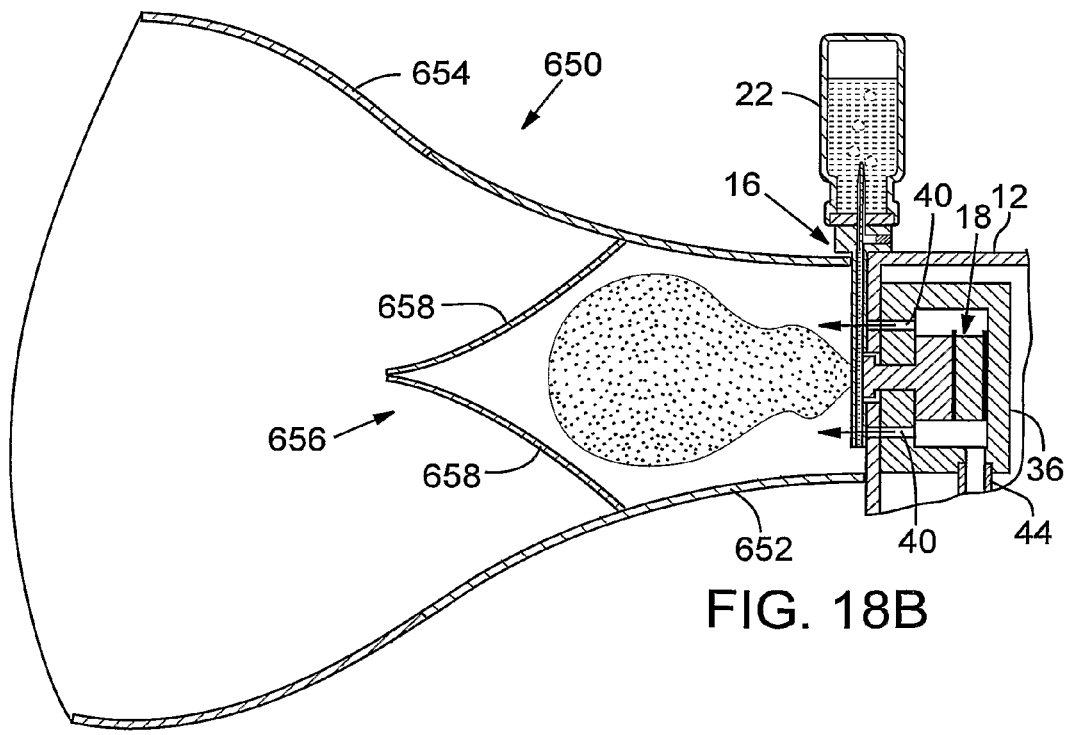

FIGS. 18A and 18B shows a patient interface 650, according to another embodiment, that includes a first portion 652 extending from the housing 12 and a second, enlarged portion 654 sized to cover the nose and mouth of a patient. The second portion 654 is made of a porous material while the first portion 652 may be made of a porous or non-porous material. The patient interface 650 is similar to the patient interface 600 of FIGS. 17A and 17B, except that the patient interface 650 includes a one-way, "duckbill" type valve 656 disposed in the first portion 652. The valve 656 includes first and second flexible sealing members 658, each of which is connected to the inside surface of the first portion 652. The sealing members 658 extend toward and contact each at their free ends so as to close the flow path from the aerosolizing element 16 to the patient when the valve is in its normal, at rest position (FIG. 18B). The sealing members 658 may be made of any of various suitable elastomeric materials. During inhalation, the sealing member 658 open to allow aerosol droplets and air to flow to the patient (FIG. 18A). During exhalation, the valve closes (FIG. 18B) to protect the aerosolizing element 16 and other re-useable components against contamination from expired particles. The patient interface 650, like the patient interface 500, preferably is disposable.

Figure 19A:
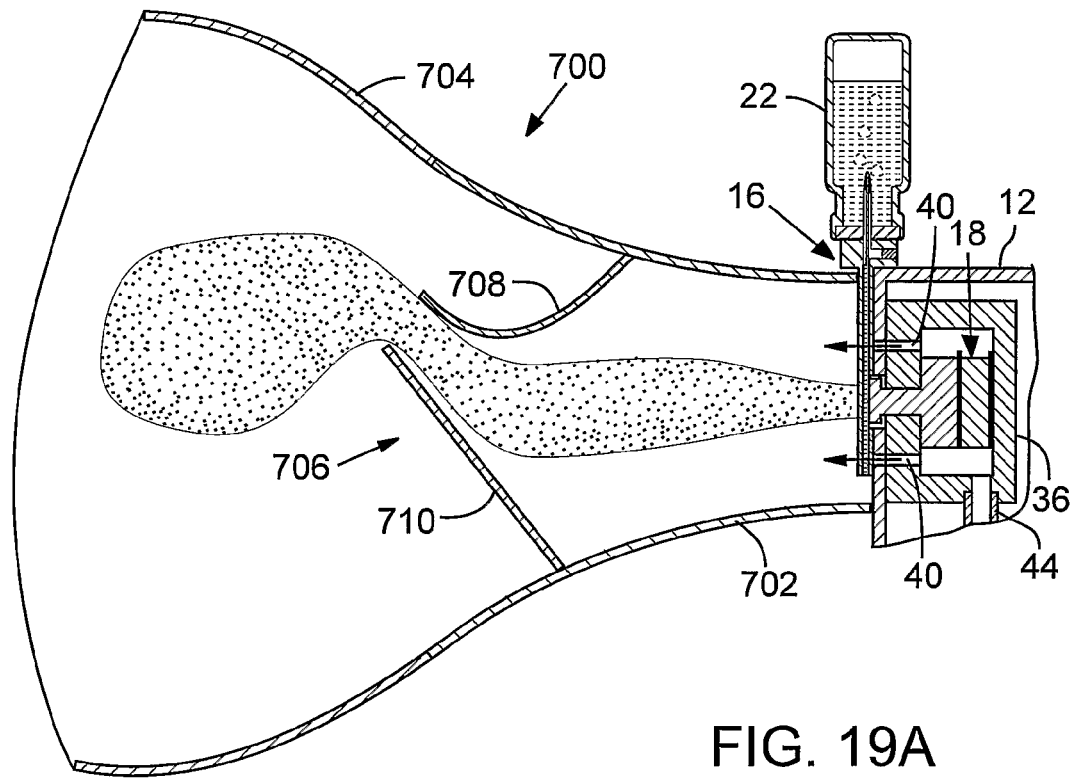
FIGS. 19A and 19B are enlarged cross-sectional views of a patient interface having a one-way valve, according to another embodiment.
Figure 19:
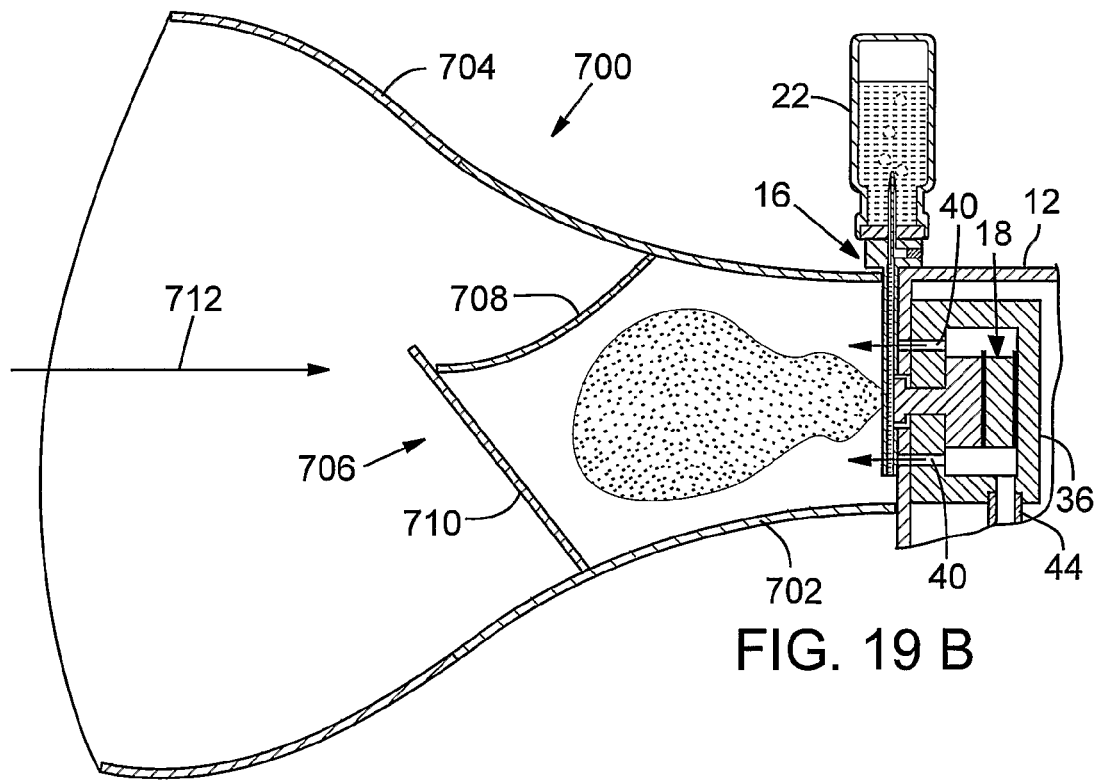

FIGS. 19A and 19B shows a patient interface 700, according to another embodiment, that includes a first portion 702 extending from the housing 12 and a second, enlarged portion 704 sized to cover the nose and mouth of a patient. The second portion 704 is made of a porous material while the first portion 702 may be made of a porous or non-porous material. The patient interface 700 includes a one-way flapper-type valve 706 that includes a flexible sealing member 708 secured at one end to the inside surface of the first portion 702. A generally rigid seating member 710 is secured to the first portion 702 opposite the flexible sealing member 708. The seating member 710 is angled away from the housing 12 and extends to a location at or above the longitudinal center of the patient interface 700 so as to shield the aerosolizing element 16 from expired particles. The valve 706 operates in similar manner to the valve 606 shown in FIGS. 17A and 17B to allow flow from the aerosolizing element 16 to the patient and restrict flow in the opposite direction during exhalation. The patient interface 700, like the patient interface 500, preferably is disposable.

Figure 20A:
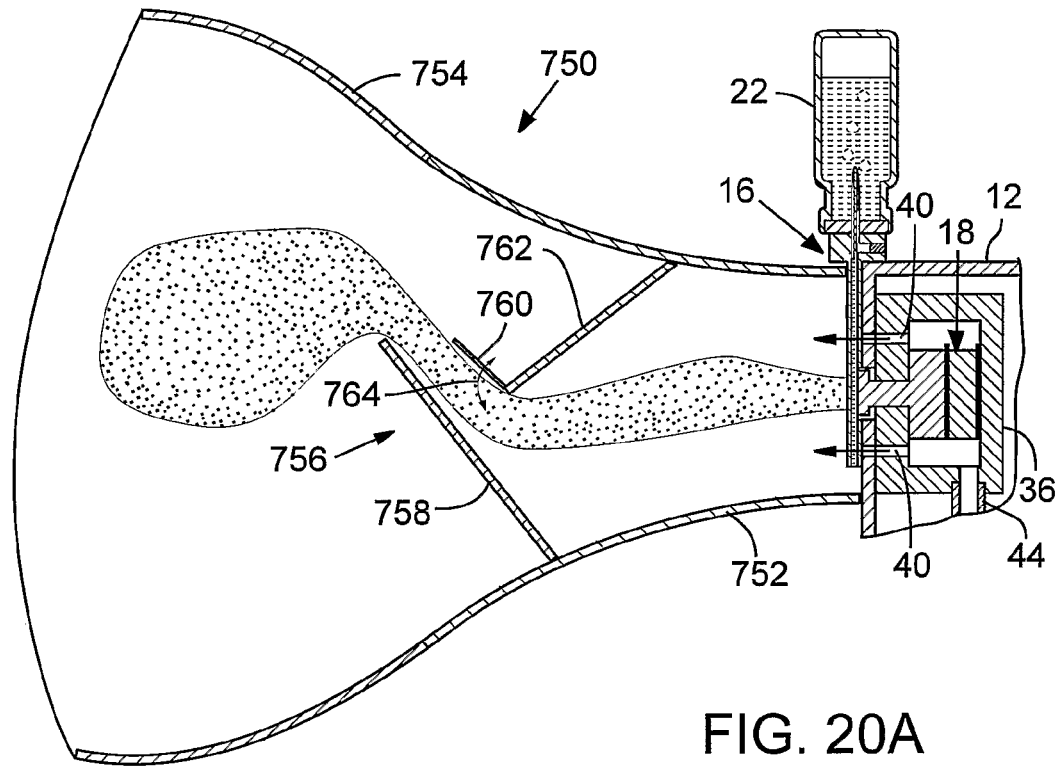
FIGS. 20A and 20B are enlarged cross-sectional views of a patient interface having a one-way valve, according to another embodiment.
Figure 20B:
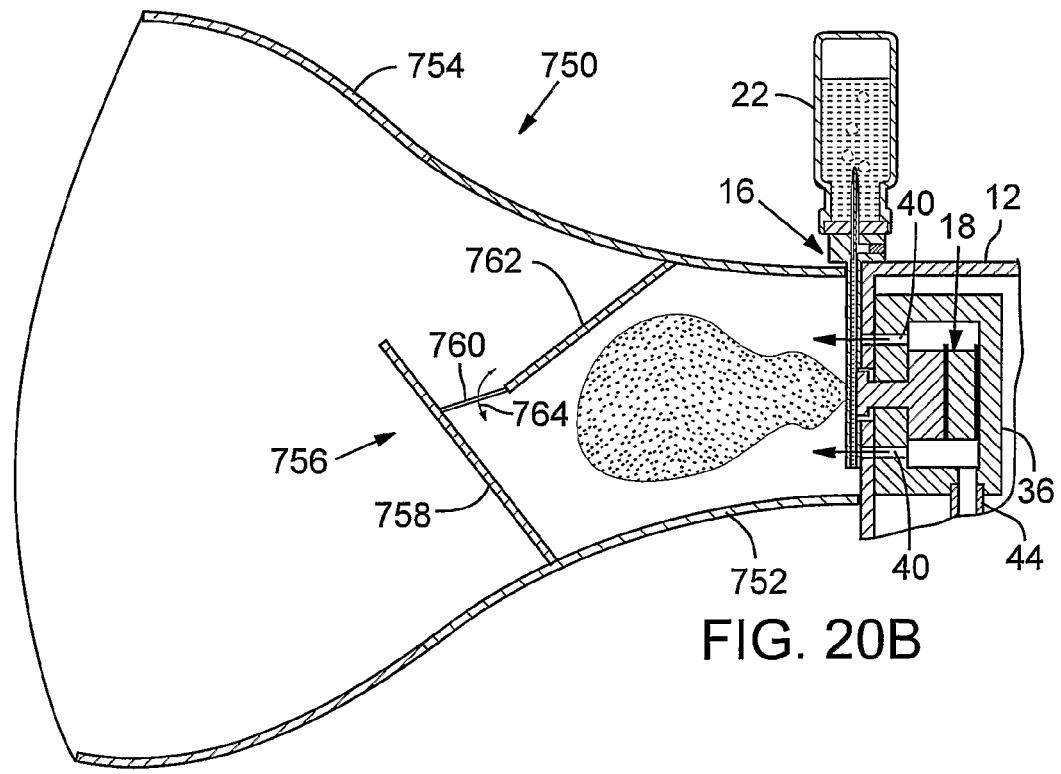

FIGS. 20A and 20B shows a patient interface 750, according to another embodiment, that includes a first portion 752 extending from the housing 12 and a second, enlarged portion 754 sized to cover the nose and mouth of a patient. The second portion 754 is made of a porous material while the first portion 752 may be made of a porous or non-porous material. The patient interface 750 includes a one-way valve 756 that includes a generally rigid seating member 758 secured to the first portion 752. A hinge assembly includes a support plate 762 secured to the first portion opposite the seating member 758 and a sealing member 760 pivotally connected to the support plate 762 for pivoting movement in the directions indicated by double-headed arrow 764. In its normal at rest position, the sealing member 760 rests against the seating member 758 (FIG. 20B) to close the valve. During inhalation, the sealing member 760 pivots upwardly and away from the seating member 758 to allow aerosol droplets and air to flow to the patient (FIG. 20A). During exhalation, the sealing member 760 returns to the closed position to restrict flow in the opposite direction (FIG. 20B).

Although the patient interfaces shown in FIGS. 11-20 are shown being used in an aerosol delivery device having an actuator 18 and an aerosolizing element 16, this is not a requirement. Accordingly, the patient interfaces can be implemented in other types of aerosol delivery systems, such as jet nebulizer systems and pneumatic aerosol delivery systems.

Figure 23:
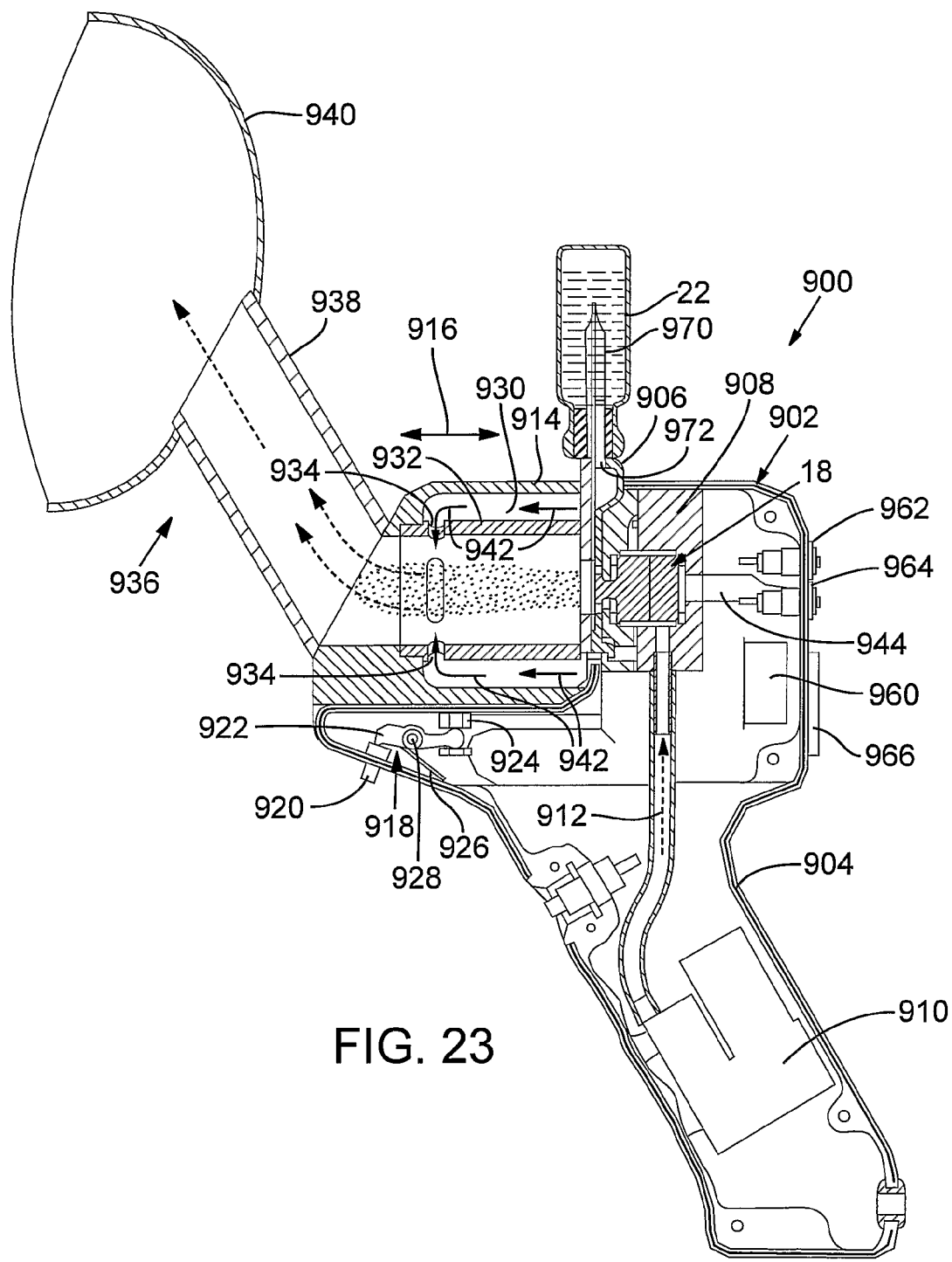
FIG. 23 is a cross-sectional view of another embodiment of an aerosol delivery device.

FIGS. 23 and 24A-24C show an aerosol delivery device 900, according to another embodiment. The aerosol delivery device 900 includes a body, or housing, 902 formed with a handle portion 904 shaped to be held in a user's hand. The housing 902 houses a removable aerosolizing element 906, an actuator 18, and an air manifold 908 substantially surrounding the actuator 18. The aerosolizing element 906 has a construction that is similar to the construction of the aerosolizing element 800 shown in FIGS. 22A-22C. Thus, components in FIGS. 23 and 24A-24C that are similar to components in FIGS. 22A-22C are given the same reference numerals and are not described further. As shown in FIG. 23, the aerosolizing device 906 further includes a piercing prong 970 extending from a venting port 972 into a vial 22.

The handle portion 904 houses an air pump 910 that is fluidly coupled to the air manifold 908 via an air conduit 912. A first indicator light 962 on the housing 902 provides a visual indication of whether an agent is being aerosolized. A second indicator light 964 provides a visual indication of whether the aerosolization rate is outside a predetermined, acceptable range. The indicator lights 962, 964 can be, for example, LEDs or lamps.

A front portion 914 of the housing 902 is mounted for sliding movement toward and away from the aerosolizing element 906, as indicated by double-headed arrow 916. In its closed, operating position (as shown in FIG. 23), the front portion 914 holds the aerosolizing element 906 firmly in place against the actuator 18. The front portion 914 can be moved to an open position spaced from the housing 902 to access the aerosolizing element 906.

A latch mechanism 918 for releasably retaining the front portion 914 in the closed position comprises a button 920 extending through the housing, a lever 922 connected to the housing by a pivot pin 928, and a latch pin 924 extending upwardly into a corresponding latch opening in the front portion 914. One end the lever 922 is coupled to the latch pin 924 and the opposite end of the lever bears against the button 920. A torsion spring 926 disposed around the pivot pin 928 biases the lever 922 in the counterclockwise direction in FIG. 23 to retain the latch pin 924 in the latch opening in the front portion 914. Depressing the button 920 moves in the lever 922 in the clockwise direction, which in turn removes the latch pin 924 from the latch opening so that the front portion 914 can be moved to the open position. The front portion 914 desirably is completely removable from the housing 902 for ease of cleaning.

The front portion 914 defines an air flow plenum 930 in fluid communication with the manifold 908 and a co-axially extending inner conduit 932 that receives aerosolized agent from the aerosolizing element 906. The inner conduit 932 is formed with one or more openings 934 in fluid communication with the air flow plenum 930. Coupled to the front portion 914 is a patient interface 936 that includes an upwardly angled extension portion 938 and a disposable face mask 940. The extension portion 938 desirably is connected to the forward portion 914 in a removable manner for ease of cleaning or for disposal.

In use, air from the air pump 910 flows into the manifold 908 via the conduit 912 to cool the actuator 18. A portion of the airflow is ducted into the internal conduit 932 via openings 98 in the aerosolizing element 906 (FIG. 24C) to assist in carrying aerosol droplets to the patient. Another portion of the airflow in the manifold 908 is ducted into the air flow plenum 930 and then into the inner conduit 932 via openings 934, as indicated by arrows 942. The airflow from the plenum 930 assists in preventing deposition of aerosol droplets on the inner conduit 932 by directing the flow of aerosol droplets away from the inner surface.

The aerosol delivery device 900 also includes an aerosolization rate monitor that is operable to monitor the rate at which an agent is being aerosolized by the aerosolizing element 906 by detecting the obscuration of a light beam passing through an aerosol plume emanating from the aerosolization element 906. Referring also to FIGS. 24A-24C, the aerosolization rate monitor includes a light source 944 (e.g., a diode laser or a light emitting diode (LED)) and a light detector, or sensor, 946 (e.g., a photodiode), both of which are coupled to the rear surface of the manifold 908. First and second passageways 948 and 950, respectively, extend between the front and rear surfaces of the manifold 908. The aerosolization element 906 includes first and second reflectors 952 and 954, respectively, positioned on opposite sides of an orifice plate 814. Each reflector 952, 954 has a reflective surface 958 positioned at approximately a 45 degree angle with respect to the first and second passageways 948, 950 in the manifold 908.

The light source 944 projects a light beam through the first passageway 948, the aerosolization element 906, and onto the reflective surface 958 of the first reflector 952. The first reflector 952 reflects the light beam across the aerosol plume emanating from the aerosolization element 906 and onto the reflective surface 958 of the second reflector 954. The second reflector 954 reflects the light beam back through the aerosolization element 906 and the second passageway 950 toward the light detector 946. The aerosolization element 906 desirably is made of a transparent material (e.g., clear plastic) to transmit the incident and reflected light beam. Alternatively, the aerosolization element 906 can be made of a non-transparent material having openings aligned with the first and second passageways 948, 950 to allow the incident and reflected light beam to pass through the aerosolization element. The reflective surfaces 958 can be formed by applying reflective paint or a layer of reflective material (e.g., reflective tape) on the reflectors 952, 954.

As the aerosol plume passes through the reflected light beam (as best shown in FIG. 24C), the light detector 946 detects the obscuration of the light beam, which corresponds to the concentration of aerosol droplets in the aerosol plume. The light detector 946 relays a signal to a controller 960 (FIG. 23), which determines the aerosolization rate. If the aerosolization rate is outside of the acceptable range, the indicator light 964 illuminates or begins flashing to provide a visual indication of this condition. The system 900 also can include a digital readout 966 (FIG. 23) mounted at a convenient location on the housing 902 to provide a digital readout of the aerosolization rate. Other indicating devices, such as an audible alarm, also can be used to provide the user information regarding the operating status of the system.

The system 900 also can be equipped with a counting device that counts or records the number of doses administered and the amount of each dose. In one implementation, for example, the controller 960 can have memory for recording dose information (e.g., number and amount of each dose) and other information regarding the operation of the system. Information recorded in the memory can be displayed on the digital readout 966. The device 900 also can include a removable memory device (e.g., a flash memory card) for storing such operating information. Additionally, a communication port (not shown) can be provided to allow operating information of the device 900 to be communicated to a general purpose computer (e.g., a laptop) via a cable or a wireless connection.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A removable aerosolizing element for use in an aerosol delivery device for aerosolizing an agent, comprising:
   a body having an exterior surface and a chamber defined therein;
   an inlet defined in the body for connection to a source of agent, the inlet being in fluidic communication with the chamber;
   agent releasing orifices defined in the body and in communication with the chamber;
   a movable element having an inner surface that defines a portion of the chamber, the movable element being capable of moving in response to an external force applied to the exterior surface, wherein the external force causes the movable element to move toward the agent releasing orifices to increase pressure in the chamber and cause agent in the chamber to be expelled through the orifices; and
   projections disposed in the chamber and maintaining a minimum spacing between the moveable element and the orifices, the projections being configured to contact the inner surface of the moveable element and an opposing inner surface of the chamber defining said orifices to maintain the minimum spacing when the external force is applied to the exterior surface.

2. The aerosolizing element of claim 1, wherein the movable portion is deformable, and the movable portion deforms under the external force to increase pressure in the chamber, thereby expelling agent from the chamber through the orifices.

3. The aerosolizing element of claim 1, wherein the movable element comprises a flexible diaphragm.

4. The aerosolizing element of claim 3, wherein the projections are on the flexible diagram.

5. The aerosolizing element of claim 3, wherein the body comprises an opening adjacent the flexible diaphragm, the opening being adapted to receive an actuator for coupling to the flexible diaphragm and applying the external force.

6. The aerosolizing element of claim 1, wherein the chamber includes an internal passageway portion in communication with the inlet and a main chamber portion generally opposite the orifices.

7. The aerosolizing element of claim 1, wherein the chamber is filled with a predetermined quantity of agent and the inlet is sealed.

8. The aerosolizing element of claim 1, further comprising a cover positioned over the inlet to reduce entry of undesired material into the chamber.

9. The aerosolizing element of claim 1, wherein the body comprises an orifice plate partially bounding the chamber generally opposite the movable element, the orifice plate defining the orifices.

10. The aerosolizing agent of claim 9, wherein the orifice plate comprises a metal foil.

11. The aerosolizing element of claim 1, wherein the chamber can be filled with agent via gravity feed from the inlet.

12. The aerosolizing element of claim 1, wherein the chamber can be filled with agent via capillary action.

13. The aerosolizing element of claim 1, wherein the projections are dimensioned to contact the inner surface of the moveable element and the opposing inner surface of the chamber when the external force is not applied to the moveable element.

14. The aerosolizing element of claim 1, wherein the external force applied to the movable member comprises vibratory oscillations causing the movable member to reciprocate and alternatingly increase pressure in the chamber to expel agent and decrease pressure to draw additional agent into the chamber.

15. The aerosolizing element of claim 1, wherein the element is pre-filled with at least a first component and a second component of an agent to be aerosolized that are mixed within the element prior to aerosolization.

16. The aerosolizing element of claim 15, wherein body comprises a first reservoir pre-filled with the first component of the agent, a second reservoir pre-filled with the second component of the agent, and a separation element disposed between the first and second reservoirs and separating the first component from the second component, the separation element being movable into the first reservoir to allow mixing of the first and second components.

17. The aerosolizing element of claim 1, wherein the body includes a needle portion shaped to receive a vial of agent and wherein an end of the needle defines the inlet.

18. The aerosolizing element of claim 1, wherein the element is disposable after use.

19. The aerosolizing element of claim 1, wherein one side of the body is adapted for direct attachment to a patient interface for conveying aerosolized agent from the orifices towards a patient.

20. The aerosolizing element of claim 1, wherein the chamber includes an air vent separate from the inlet.

21. The aerosolizing element of claim 1, wherein:
the aerosol delivery device comprises an actuator that applies the external force to the movable element to cause the agent to be expelled through the orifices; and
the body is configured to prevent the agent from contacting the actuator.

22. The aerosolizing element of claim 1, further comprising at least one airflow passageway extending through the body such that air flowing through the passageway can carry the expelled agent away from the element.

23. The aerosolizing element of claim 22, wherein the airflow passageway comprises an inlet defined in one side of the body and an outlet defined in an opposing side of the body, the outlet being offset from the inlet.

24. The aerosolizing element of claim 1, wherein the body comprises first and second reflective surfaces positioned on opposite sides of the orifices such that a light beam passing through the element is reflected by the first reflective surface to extend in front of the orifices and onto the second reflective surface, which reflects the light beam back through the element.

25. The aerosolizing element of claim 24, wherein the body comprises a transparent material that transmits the light beam.

26. The aerosolizing element of claim 1, wherein the projections are formed on the moveable element.

27. The aerosolizing element of claim 1, wherein the projections have a height of about 0.1 mm equal to the minimum spacing of the chamber.

28. The aerosolizing element of claim 1, wherein the orifices are formed by laser drilling.

29. The aerosolizing element of claim 1, wherein the projections are configured to allow agent to flow through the chamber when the projections are in contact with the inner surface of the movable element and the opposing inner surface of the chamber.

30. The aerosolizing element of claim 1, in combination with the aerosol delivery device, the aerosol delivery device comprising an ultrasonic horn coupled to the moveable element and comprising an actuator and a motion transmitting member coupling the actuator to the moveable element for transferring vibratory motion of the actuator to the moveable element.

* * * * *